US011203754B2

(12) United States Patent
Greco et al.

(10) Patent No.: US 11,203,754 B2
(45) Date of Patent: Dec. 21, 2021

(54) MICRORNA COMPOSITIONS AND METHODS OF MAKING AND USING SAME

(71) Applicant: Advanced ReGen Medical Technologies, LLC, Houston, TX (US)

(72) Inventors: Steven John Greco, Houston, TX (US); Pranela Rameshwar, Newark, NJ (US)

(73) Assignee: Advanced ReGen Medical Technologies, LLC, Houston, TX (US)

( * ) Notice: Subject to any disclaimer, the term of this patent is extended or adjusted under 35 U.S.C. 154(b) by 0 days.

(21) Appl. No.: 15/581,705

(22) Filed: Apr. 28, 2017

(65) Prior Publication Data

US 2017/0314019 A1 Nov. 2, 2017

Related U.S. Application Data

(60) Provisional application No. 62/482,465, filed on Apr. 6, 2017, provisional application No. 62/329,486, filed on Apr. 29, 2016.

(51) Int. Cl.
*C12N 15/113* (2010.01)
*C12N 15/85* (2006.01)

(52) U.S. Cl.
CPC ............ *C12N 15/113* (2013.01); *C12N 15/85* (2013.01); *C12N 2310/141* (2013.01); *C12N 2320/31* (2013.01)

(58) Field of Classification Search
CPC .. C12N 15/113; C12N 15/85; C12N 2320/31; C12N 2310/141; A61P 43/00
See application file for complete search history.

(56) References Cited

U.S. PATENT DOCUMENTS

| | | | |
|---|---|---|---|
| 2,984,164 | A | 5/1961 | Melle |
| 3,083,939 | A | 4/1963 | Gallagher, Jr. |
| 3,122,333 | A | 2/1964 | Steele et al. |
| 3,436,081 | A | 4/1969 | Ungar |
| 8,257,973 | B2 | 9/2012 | Park et al. |
| 8,747,915 | B1 | 6/2014 | Giampapa |
| 8,945,558 | B2 | 2/2015 | Kobara |
| 9,828,603 | B2 | 11/2017 | Marbán et al. |
| 9,994,814 | B2 | 6/2018 | Giampapa |
| 10,717,981 | B2 | 7/2020 | Greco et al. |
| 10,772,911 | B2 | 10/2020 | Greco et al. |
| 2002/0033370 | A1 | 3/2002 | Bainbridge et al. |
| 2002/0046975 | A1 | 4/2002 | Langley et al. |
| 2004/0199935 | A1 | 10/2004 | Chapman |
| 2005/0158285 | A1 | 7/2005 | Giampapa |
| 2006/0188986 | A1 | 8/2006 | Millar et al. |
| 2007/0025973 | A1 | 2/2007 | Fitzsimmons et al. |
| 2007/0196918 | A1 | 8/2007 | Sayre et al. |
| 2008/0213812 | A1 | 9/2008 | Andrews et al. |
| 2008/0260704 | A1 | 10/2008 | Riordan et al. |
| 2008/0268429 | A1 | 10/2008 | Pietrzkowski |
| 2009/0011004 | A1 | 1/2009 | Lutz et al. |
| 2009/0317369 | A1 | 12/2009 | Hosoda et al. |
| 2009/0318345 | A1 | 12/2009 | Fibbe et al. |
| 2010/0273255 | A1* | 10/2010 | Tuschl ................ C12N 15/113 435/325 |
| 2011/0003008 | A1 | 1/2011 | Lim |
| 2011/0177054 | A1 | 7/2011 | Gibbings et al. |
| 2011/0258716 | A1 | 10/2011 | Baltimore et al. |
| 2011/0300112 | A1 | 12/2011 | Marbán et al. |
| 2012/0093385 | A1 | 4/2012 | Yokosawa et al. |
| 2012/0093885 | A1 | 4/2012 | Sahoo et al. |
| 2012/0253102 | A1 | 10/2012 | Marbán et al. |
| 2012/0258093 | A1 | 10/2012 | Butler-Browne et al. |
| 2012/0321723 | A1 | 12/2012 | Bruno et al. |
| 2013/0017176 | A1 | 1/2013 | Hosoda et al. |
| 2013/0143314 | A1 | 6/2013 | Shiels et al. |
| 2013/0177593 | A1 | 7/2013 | Gunn et al. |
| 2013/0195899 | A1 | 8/2013 | Ichim et al. |
| 2013/0209528 | A1 | 8/2013 | Levi et al. |
| 2013/0236428 | A1 | 9/2013 | Giampapa |
| 2013/0302285 | A1 | 11/2013 | Fong et al. |
| 2013/0336935 | A1 | 12/2013 | Niedernhofer et al. |
| 2014/0004601 | A1 | 1/2014 | Lim |
| 2014/0031256 | A1 | 1/2014 | Lim |
| 2014/0088006 | A1 | 3/2014 | Tsyrolva et al. |
| 2014/0120066 | A1 | 5/2014 | Yeghiazarians et al. |

(Continued)

FOREIGN PATENT DOCUMENTS

| | | |
|---|---|---|
| CA | 2845280 | 2/2012 |
| CN | 102573856 A | 7/2012 |

(Continued)

OTHER PUBLICATIONS

Pie et al. (PLOS One (2012) vol. 7(12), article # e50746, 14 pages). (Year: 2012).*
Sugihara et al. (PLOS ONE (2019) 14(5)e:0217394; p. 1-17). (Year: 2019).*
Qui et al. (Oncol. Lett. (Epub Oct. 2016) 12(6):5036-5042). (Year: 2016).*
Foreign communication from a related counterpart application—International Search Report and Written Opinion, PCT/US2017/030117, dated Sep. 12, 2017, 12 pages.
Guan, X, et al., "miR-223 regulates adipogenic and osteogenic differentiation of mesenchymal stem cells through a C/EBPs/miR-223/FGFR2 regulatory feedback loop," Stem Cells, 2015, pp. 1589-1600, vol. 33, AlphaMed Press.
Shmazaki, T., et al., "Heterochronic microRNAs in temporal specification of neural stem cells: application toward rejuvenation," NPJ Aging and Mechanisms of Disease, Jan. 7, 2016, pp. 1-6, vol. 2, No. 15014, Japanese Society of Anti-Aging Medicine/Macmillan Publishers Limited.

(Continued)

*Primary Examiner* — J. E. Angell
(74) *Attorney, Agent, or Firm* — Knobbe Martens Olson & Bear LLP

(57) ABSTRACT

A method comprising administering to a subject a composition comprising an isolated microRNA having a sequence selected from the group consisting of miR-19a-3p (SEQ ID NO:1); miR-103a-3p (SEQ ID NO:2); miR-106b-5p (SEQ ID NO:3); miR-146a-5p (SEQ ID NO:4); miR-223-5p (SEQ ID NO:5); miR-4497 (SEQ ID NO:6); miR-1303 (SEQ ID NO:7); miR-619-5p (SEQ ID NO:8); miR-1273f (SEQ ID NO:9); miR-7851-3p (SEQ ID NO:10); a functional variant thereof; and combinations thereof.

12 Claims, 3 Drawing Sheets

Specification includes a Sequence Listing.

(56) References Cited

U.S. PATENT DOCUMENTS

| | | | |
|---|---|---|---|
| 2014/0121171 A1 | 5/2014 | Muñoz-Cánoves et al. | |
| 2014/0127284 A1 | 5/2014 | Cheresh | |
| 2015/0023935 A1 | 1/2015 | Giampapa | |
| 2015/0174166 A1 | 6/2015 | Giampapa | |
| 2015/0203844 A1 | 7/2015 | Marbán et al. | |
| 2015/0273113 A1 | 10/2015 | Marbán et al. | |
| 2015/0328263 A1 | 11/2015 | Kaushal | |
| 2015/0367063 A1 | 12/2015 | Kimura | |
| 2016/0108370 A1 | 4/2016 | Greco et al. | |
| 2016/0145571 A1 | 5/2016 | Giampapa | |
| 2016/0243171 A1 | 8/2016 | Shiels et al. | |
| 2017/0087087 A1 | 3/2017 | Leonard et al. | |
| 2017/0107581 A1 | 4/2017 | Kawauchi et al. | |
| 2017/0130275 A1* | 5/2017 | Kondou | C12Q 1/6886 |
| 2017/0173076 A1 | 6/2017 | Greco et al. | |
| 2017/0275699 A1 | 9/2017 | Kawauchi et al. | |
| 2017/0290860 A1 | 10/2017 | Marbán et al. | |
| 2017/0304368 A1 | 10/2017 | Marbán et al. | |
| 2017/0314019 A1 | 11/2017 | Greco et al. | |
| 2018/0100149 A1 | 4/2018 | Marbán et al. | |
| 2018/0360878 A1 | 12/2018 | Giampapa | |
| 2018/0371465 A1 | 12/2018 | Hinkle | |
| 2019/0000888 A1 | 1/2019 | Marbán et al. | |

FOREIGN PATENT DOCUMENTS

| | | |
|---|---|---|
| CN | 109475645 A | 3/2019 |
| EP | 2 687 219 | 1/2014 |
| EP | 2 823 039 | 1/2015 |
| EP | 2 984 164 | 2/2016 |
| EP | 3 083 939 | 10/2016 |
| EP | 3 122 333 | 2/2017 |
| EP | 3 436 081 | 2/2019 |
| JP | 2017510582 A | 4/2017 |
| JP | 6353073 B2 | 7/2018 |
| JP | 6471302 B2 | 2/2019 |
| KR | 10-2008-0049917 | 6/2008 |
| KR | 20170139701 A | 5/2017 |
| TW | 201739458 A | 11/2017 |
| WO | WO 2004/048555 | 6/2004 |
| WO | WO 2006/007529 | 1/2006 |
| WO | WO 2006/052925 | 5/2006 |
| WO | WO 2007/016245 | 2/2007 |
| WO | WO 2007/109223 | 9/2007 |
| WO | WO 2008/066330 | 6/2008 |
| WO | WO 2008/103135 A2 | 8/2008 |
| WO | WO 2009/011546 | 1/2009 |
| WO | WO 2009/086425 | 7/2009 |
| WO | WO 2009105044 | 8/2009 |
| WO | WO 2011/029903 | 3/2011 |
| WO | WO 2012/020307 | 2/2012 |
| WO | WO 2012/149557 | 11/2012 |
| WO | WO 2012/162741 | 12/2012 |
| WO | WO 2013/048734 | 4/2013 |
| WO | WO 2013066368 | 5/2013 |
| WO | WO 2013/134513 | 9/2013 |
| WO | WO 2013/170170 | 11/2013 |
| WO | WO 2014/013258 | 1/2014 |
| WO | WO 2014/028493 | 2/2014 |
| WO | WO 2014028493 A2 | 2/2014 |
| WO | WO 2014028493 A3 | 2/2014 |
| WO | WO 2014/036429 | 3/2014 |
| WO | WO 2014/053105 | 4/2014 |
| WO | WO 2014/125276 | 8/2014 |
| WO | WO 2014/169077 | 10/2014 |
| WO | WO 2015/022545 | 2/2015 |
| WO | 2015052527 A1 | 4/2015 |
| WO | WO 2015/073625 | 5/2015 |
| WO | WO 2015/085096 | 6/2015 |
| WO | WO 2015095794 | 6/2015 |
| WO | WO 2015/120150 | 8/2015 |
| WO | WO 2015/148534 | 10/2015 |
| WO | WO 2015/182781 A1 | 12/2015 |
| WO | WO 2015/190542 A1 | 12/2015 |
| WO | WO 2016/054591 | 4/2016 |
| WO | WO 2016/057560 | 4/2016 |
| WO | WO 2017/190000 | 4/2017 |
| WO | WO 2009/011546 | 1/2019 |
| WO | WO 2019/028223 | 2/2019 |
| WO | WO 2019/143847 A1 | 7/2019 |
| WO | WO 2020/190888 | 9/2020 |

OTHER PUBLICATIONS

Hsieh, J.-Y., et al., "miR-146a-5p circuitry uncouples cell proliferation and migration, but not differentiation, in human mesenchymal stem cells," Nucleic Acids Research, 2013, pp. 9753-9763, vol. 41, No. 21.

Filing Receipt and Specification of U.S. Appl. No. 62/329,486, filed Apr. 29, 2016, entitled "Microrna Compositions and Methods of Making and Using Same," 46 pages.

Filing Receipt and Specification of U.S. Appl. No. 62/482,465, filed Apr. 6, 2017, entitled "Microrna Compositions and Methods of Making and Using Same," 53 pages.

Filing receipt and Specification of International Application No. PCT/US2017/030117 filed Apr. 28, 2017, entitled "Microrna Compositions and Methods of Making and Using Same," 51 Pages.

Ajijola et al., "Ventricular Tachycardia in Ischemic Heart Disease Substrates", Indian Heart Journal, 2014, pp. S24-S34, S28 & S30, vol. 66, Supplement 1.

Aminzadeh et al., "Heart-Derived Cell Therapy for Duchenne Cardiomyopathy: Cardiosphere-Derived Cells and their Exosomes Improve Function, Restore Mitochondrial Integrity and Reverse Degenerative Changes in the Hearts of Mdx Mice", Circulation Research, Decembers, 2014, vol. 115, No. 12, 24248, pp. E90-E91.

Archundia, A., et al., "Direct cardiac injection of G-CSF mobilized bone-marrow stem-cells improves ventricular unction in old myocardial infarction," Life Sciences, Apr. 21, 2005, pp. 279-283, vol. 78, Elsevier Inc.

Baglio, S. R., et al.,. "Mesenchymal stem cell secreted vesicles provide novel opportunities in (stem) cell-free Therapy," Frontiers in Physiology, Sep. 6, 2012, pp. 1-11, vol. 3.

Beelen, Dietrich W., et al., "Transplantation of Filgrastim-Mobilized Peripheral Blood Stem Cells From HLA-identical Sibling or Alternative Family Donors in Patients With Hematologic Malignancies: A Prospective Comparison on Clinical Outcome, Immune Reconstitution, and Hematopoietic Chimerism," Blood, Dec. 15, 1997, pp. 4725-4735, vol. 90 No. 12, The American Society of Hematology.

Conboy, Irina M. et al., "Rejuvenation of aged progenitor cells by exposure to a young systemic environment", Nature, vol. 433, No. 7027, Feb. 17, 2005, pp. 760-764.

Chen et al., "Mesenchymal Stem Cell Secretes Microparticles Enriched in Pre-MicroRNAs", Nucleic Acids Research, 2010, vol. 38, No. 1, pp. 215-224.

Chimenti et al., "Relative Roles of Direct Regeneration Versus Paracrine Effects of Human Cardiosphere-Derived Cells Transplanted Into Infarcted Mice", Circulation Research, Mar. 19, 2010, vol. 106, pp. 971-980.

De Bakker et al., "Slow Conduction in the Infarcted Human Heart 'Zigzag' Course of Activation", Circulation, Sep. 1993, pp. 915-926, vol. 88, No. 3.

De Couto et al., "Macrophages Mediate Cardioprotective Cellular Postconditioning in Acute Myocardial Infarction", The Journal of Clinical Investigation, Jul. 27, 2015, vol. 125, No. 8, pp. 3147-3162.

Iglesias, D. M., "Stem Cell Microvesicles Transfer Cystinosin to Human Cystinotic Cells and Reduce Cystine Accumulation in Vitro," PLOS ONE, Aug. 13, 2012, pp. 1-9, vol. 7, No. 8.

Grigorian-Shamagian et al., "Cardiac and Systemic Rejuvenation After Cardiosphere-Derived Cell Therapy in Senescent Rats", European Heart Journal, Oct. 14, 2017, vol. 38, No. 39, pp. 2957-2967.

Halley-Stott, Richard P., et al., "Nuclear reprogramming," Development at a Glance, 2013, vol. 2468-2471, The Company of Biologists Ltd.

Hine et al., "NRF2 and the Phase II Response in Acute Stress Resistance Induced by Dietary Restriction", Journal of Clinical & Experimental Pathology, Jun. 19, 2012, vol. S4, No. 4, pp. 1-33.

(56) References Cited

OTHER PUBLICATIONS

Hoetzenecker, Konrad, et al., "Mononuclear cell secretome protects from experimental autoimmune myocarditis," European Heart Journal, Jan. 15, 2013, pp. 676-685, vol. 36, No. 11.
Hu et al., "MicroRNA-210 as a Novel Therapy for Treatment of Ischemic Heart Disease", Circulation, Sep. 14, 2010, vol. 122, Supplement 11, S124-S131, pp. 17.
Ibrahim et al., "Exosomes as Critical Agents of Cardiac Regeneration Triggered by Cell Therapy", Stem Cell Reports, May 6, 2014, vol. 2, pp. 606-619.
Ibrahim, A., et al. "Exosomes: Fundamental Biology and Roles in Cardiovascular Physiology," Annu. Rev. Physiol., 78, 68-83, 2017.
Ibrahim et al., "Microrna-Containing Exosomes from Cardiosphere-Derived Cells Stimulate Cardiomyocyte Proliferation and Angiogenesis in Vitro, and Improve Functional Recovery after Myocardial Infarction in Mice", Circulation, 2012, vol. 126, Abs. 14697, pp. 4.
Ibrahim et al., "Role of Exosomes and Their MicroRNA Constituents in Mediating the Therapeutic Benefits of Human Cardiosphere-Derived Cells in Vitro and in Mice with Myocardial Infarction", Circulation, Nov. 26, 2013, vol. 128, No. 22, Abs. 19186, pp. 2.
Jayawardena et al., MicroRNA-Mediated In Vitro and In Vivo Direct Reprogramming of Cardiac Fibroblasts to Cardiomyocytes, Circulation Research, 2012, vol. 110, No. 11, pp. 1465-1473.
Kamdar et al., "Dystrophin-Deficient Cardiomyopathy", Journal of the American College of Cardiology, 2016, vol. 67, No. 21, pp. 2533-2546.
Kim, Mi Jung, et al., "Age-related Deterioration of Hematopoietic Stem Cells," International Journal of Stem Cells, 2008, 99. 55-63, vol. 1, No. 1.
Kooijmans et al., "PEGylated and Targeted Extracellular Vesicles Display Enhanced Cell Specificity and Circulation Time", Journal of Controlled Release, 2016, vol. 224, pp. 77-85.
Kordelas, L., et al., "MSC-derived exosomes: a novel tool to treat therapy-refractory graft-versus-host disease," Leukemia, Jan. 21, 2014, pp. 970-973, vol. 28, Macmillan Publishers Limited.
Kroschinsky, Frank, et al., "Single-dose pegfilgrastim for the mobilization of allogeneic CD34+ peripheral blood progenitor cells in healthy family and unrelated donors," Haematologica, Dec. 1, 2005, pp. 1665-1671, vol. 90, No. 12, Ferrata Storti Foundation.
Lai et al., "Exosome Secreted by MSC Reduces Myocardial Ischemia/Reperfusion Injury", Stem Cell Research, 2010, vol. 4, pp. 214-222.
Lavasani, Mitra, et al., "Muscle-derived stem/ progenitor cell dysfunction limits healthspan and lifespan in a murine progeria model," Nature Communications, Jan. 3, 2012, pp. 1-12, vol. 3, No. 608, Macmillan Publishers Limited.
Lee et al., "Intramyocardial Injection of Autologous Cardiospheres or Cardiosphere-Derived Cells Preserves Function and Minimizes Adverse Ventricular Remodeling in Pigs With Heart Failure Post-Myocardial Infarction", Journal of the American College of Cardiology, Jan. 25, 2011, vol. 57, No. 4, pp. 455-465.
Li et al., "Direct Comparison of Different Stem Cell Types and Subpopulations Reveals Superior Paracrine Potency and Myocardial Repair Efficacy with Cardiosphere-Derived Cells", Journal of American College of Cardiology, 2012, vol. 59, No. 10, pp. 942-953.
Li, Shu-Hong, et al., "Reconstitution of aged bone marrow with young cells repopulates cardiac-resident bone arrow :derived progenitor cells and prevents cardiac dysfunction after a myocardial infarction", European Heart Journal, Apr. 16, 2012, pp. 1157-1167, vol. 34, No. 15.
Mccullagh, Karl J A: "Can a young muscle's stem cell secretome prolong our lives?", Stem Cell Research & Therapy, vol. 3, May 2012.
Melamed, Doran, et al., "Aging and neoteny in the B lineage," Blood, 2012, vol. 120, No. 20.
Middleton et al., "Newt Cells Secrete Extracellular Vesicles with Therapeutic Bioactivity in Mammalian Cardiomyocytes", Journal of Extracellular Vesicles, 2018, vol. 7, pp. 1-15.
Mildner, Michael, et al., "Secretome of Peripheral Blood Mononuclear Cells Enhances Wound Healing," PLoS ONE, Mar. 22, 2013, pp. 1-8, vol. 8, No. 3.
Mittelbrunn, Maria, et al., "Unidirectional transfer of MicroRNA-loaded exosomes from T cell to antigen-presenting cells," Nature Communications, 2011, vol. 2, Article No. 282, 10 pages.
Ousaka et al., "Abstract 13881: Cardiac Progenitor Cell Infusion in Patients With Univentricular Heart Diseases in Heart Failure With Preserved Ejection Fraction", Circulation, Abstract 13881, 2015, vol. 132, <http://circ.ahajournals.org/content/132/Suppl_3/A13881.short>.
Rando, Thomas A., et al., "Aging, Rejuvenation, and Epigenetic Reprogramming: Resetting the Aging Clock," Cell, Jan. 20, 2012, vol. 148, pp. 46-57, Elsevier Inc.
Ratajczak M Z et al: "Pivotal role of paracrine effects in stem cell therapies in regenerative medicine: can we translate stem cell-secreted paracrine factors and microvesicles into better therapeutic strategies?", Leukemia (Basingstoke), vol. 26, No. 6, Jun. 2012.
RATHORE (2011, Preparative Biochemistry and Biotechnology, 41 :398-421).
Reiffel, James A., MD, FACC, "Ten Pearls for the Use of Antiarrhythmic Drugs for Atrial Fibrillation", Aug. 17, 2012, Retrieved from <http://www.acc.org/latest-in-cardiology/articles/2014/07/18/15/12/ten-pearls-for-the-use-of-antiarrhythmic-drugs-for-atrial-fibrillation>, pp. 17.
Scaria et al., "Host-Virus Genome Interactions: Marco Roles for MicroRNAs", Cellular Microbiology, 2007, vol. 9, No. 12, pp. 2784-2794.
Sharma et al., "Cardiosphere Derived Cells from Pediatric End-Stage Heart Failure Patients Have Enhanced Functional Activity due to the Heat Shock Response Regulating the Secretome", Stem Cells, Apr. 2015, pp. 1213-1229, vol. 33, No. 4.
Shen, Jinhui, et al., "Transplantation of mesenchymal stem cells from young donors delays aging in mice," Scientific Reports, 2011, vol. 1, Article No. 67, 8 pages.
Simonsson, Stina, et al., "DNA demethylation is necessary for the epigenetic reprogramming of somatic cell nuclei," Nature Cell Biology, Oct. 2004, vol. 6, No. 10, pp. 984-990, Nature Publishing Group.
Singhal, Nishant, et al., "Chromatin-Remodeling Components of the BAF Complex Facilitate Reprogramming," Cell, Jun. 11, 2010, vol. 141, pp. 943-955, Elsevier Inc.
Sun, Yun, et al., "Rescuing replication and osteogenesis of aged mesenchymal stem cells by exposure to a young extracellular matrix," The FASEB Journal, May 2011, vol. 25, No. 5, pp. 1474-1485.
Tatsumi, Kimiko et al.: "Granulocyte-Colony Stimulation Factor Increases Donor Mesenchymal Stem Cells in Bone Marrow and Their Mobilization Into Peripheral Circulation but Does Not Repair Dystrophic Heart After Bone Marrow Transplantation", Gire J, 2008.
Tseliou et al., "Allogeneic Cardiospheres Safely Boost Cardiac Function and Attenuate Adverse Remodeling After Myocardial Infarction in Immunologically Mismatched Rat Strains", Journal of the American College of Cardiology, Mar. 12, 2013, vol. 61, No. 10, pp. 1108-1119.
Vrijsen et al., "Cardiomyocyte Progenitor Cell-Derived Exosomes Stimulate Migration of Endothelial Cells", Journal of Cellular and Molecular Medicine, 2010, vol. 14, No. 5, pp. 1064-1070.
Yu, B., et al., "Exosomes Derived from Mesenchymal Stem Cells," International Journal of Molecular Sciences, Mar. 17, 2014, pp. 4142-4157, vol. 15.
U.S. Appl. No. 16/250,940, filed Jun. 17, 2019 including prosecution history.
U.S. Appl. No. 14/577,978, filed Dec. 19, 2014 including prosecution history.
U.S. Appl. No. 16/111,832, filed Aug. 24, 2018 including prosecution history.
U.S. Appl. No. 13/785,691, filed Mar. 5, 2013 including prosecution history.
U.S. Appl. No. 14/509,523, filed Oct. 8, 2014 including prosecution history.

(56) References Cited

OTHER PUBLICATIONS

U.S. Appl. No. 14/922,353, filed Oct. 26, 2015 including prosecution history.
U.S. Appl. No. 15/128,660, filed Sep. 23, 2016 including prosecution history.
U.S. Appl. No. 14/889,942, filed Nov. 9, 2015 including prosecution history.
Baker, Darren J. et al., "Clearance of p16Ink4a-positive senescent cells delays ageing-associated disorders," Nature (Nov. 1, 2011) vol. 479, No. 7372, pp. 232-236.
Bougel, S. et al., "PAX5 activates the transcription of the human telomerase reverse transcriptase gene in B cells," J. Pathol. (2010) vol. 220, No. 1, pp. 87-96.
He, X. et al., "Human Fibroblast Reprogramming to Pluripotent Stem Cells Regulated by the miR19a/b-PTEN Axis," PLOS One (Apr. 16, 2014) vol. 9, No. 4, p. e95213.
Jurmeister, S. et al., "MicroRNA-200c represses migration and invasion of breast cancer cells by targeting actin-regulatory proteins FHOD1 and PPM1F," Mol. Cell. Biol. (Feb. 2012) vol. 32, No. 3, pp. 633-651.
Lam et al., "siRNA Versus MiRNA as Therapeutics for Gene Silencing," Molecular Therapy—Nucleic Acids (2015) vol. 4, pp. 1-20.
Li, Zhonghan et al., "Small RNA-mediated regulation of iPS cell generation," EMBO Journal (Feb. 1, 2011) vol. 30, pp. 823-834.
Liang, J., et al., "MicroRNA-103a inhibits gastric cancer cell proliferation, migration and invasion by targeting c-Myb," Cell Proliferation (Dec. 22, 2014) vol. 48, No. 1, pp. 78-85.
Lu, D., et al., "The miR-155-PU.1 axis acts on Pax5 to enable efficient terminal B cell differentiation," J. Exp. Med. (2014) vol. 211, No. 11, pp. 2183-2198.
Melief, Sara et al., "Multipotent stromal cells skew monocytes towards an anti-inflammatory interleukin-10-producing phenotype by production of interleukin-6," Haematologica (Jan. 24, 2013) 98(6): pp. 888-895.
NCBI Reference Sequence No. NM_014634.3, "*Homo sapiens* protein phosphatase, Mg2+/Mn2+ dependent 1F (PPM1F), mRNA," (Oct. 16, 2017).
NCBI Reference Sequence No. NM_016734.2, "*Homo sapiens* paired box 5 (PAX5), transcript variant 1, mRNA," (Nov. 30, 2017).
NCBI Reference Sequence No. NR_030350.1, "*Homo sapiens* microRNA619 (MIR619), microRNA," (Jun. 26, 2017).
Niyazova et al., "The interaction of miRNAs with mRNAs of the cell cycle genes in lung cancer," Proceedings of the Moscow Conference on Computational Molecular Biology (MCCMB'15) (Jul. 2015) XP55595996.
PPM 1 F Wikipedia downloaded from https ://en. wikipedia .org/ wiki/P PM 1 F on Sep. 9, 2019.
Rejenevie Therapeutics [rejenevie]. (published on May 15, 2019). "The Science Behind Immune Restoration," [Video file]. Retrieved from https://youtu.be/alKFhloo-L4, (transcript provided herewith).
Rejenevie Therapeutics [rejenevie], (published Jun. 10, 2019). "10 Steps to Immune Restoration with Rejenevie," [Video file]. Retrieved from https://youtu.be/ulCaTgjXXf8, (transcript provided herewith).
Rejenevie Therapeutics [rejenevie], (published May 10, 2019). "FAQs For Patients: Restoration & Young Donors," [Video file]. Retrieved from https://youtu.be/GOm_Q5nTbPM, (transcript provided herewith).
Rejenevie Therapeutics [rejenevie], (published May 10, 2019). "FAQs For Patients: Okyanos & Post-Treatment Testing," [Video file]. Retrieved from https://youtu.be/YU-v4yic36l, (transcript provided herewith).
Rejenevie Therapeutics [rejenevie], (published May 10, 2019). "FAQs For Patients: Screening, Mobilization & Treatment," [Video file]. Retrieved from https://youtu.be/V3NIJ-emB1U, (transcript provided herewith).
Rejenevie Therapeutics [rejenevie]. (published on May 23, 2019)." The Science Behind The Transwell System," [Video file]. Retrieved from https://youtu.be/Y75UXv747IQ, (transcript provided herewith).
Suh, Mi-Ra, et al., "Human embryonic stem cells express a unique set of mircoRNAs," Development Biology (May 6, 2004) vol. 270, No. 2, pp. 488-498.
Tu, S.H. et al., "Protein phosphatase Mg2+/Mn2+ dependent 1F promotes smoking-induced breast cancer by inactivating phosphorylated-p53-induced signals," Oncotarget (Oct. 18, 2016) vol. 7, No. 47, pp. 77516-77531.
Yu, Bin et al., "Exosomes secreted from GATA-4 overexpressing mesenchymal stem calls serve as a reservoir of anti-apoptotic microRNAs for cardioprotection," International Journal of Cardiology (Dec. 23, 2014) vol. 182, pp. 349-360.
Yu, Ge et al., "MicroRNA-19a targets tissue factor to inhibit colon cancer cells migration and invasion," Molecular and Cellular Biochemistry (May 12, 2013) vol. 380, No. 1-2, pp. 239-247.
Zhang et al., "miR-1303 Targets Claudin-18 Gene to Modulate Proliferation and Invasion of Gastric Cancer Cells," Digestive Diseases and Sciences (Mar. 20, 2014) vol. 59, No. 8, pp. 1754-1763, XP55595270.
International Search Report and Written Opinion dated Jul. 26, 2013 for PCT/US2013/029633.
International Search Report and Written Opinion dated Aug. 16, 2014 for PCT/US2014/033564.
International Preliminary Report on Patentability dated Sep. 9, 2014 for PCT/ US2013/029633.
International Search Report and Written Opinion dated Mar. 31, 2015 for PCT/US2014/071667.
International Search Report and Written Opinion dated Jun. 30, 2015 for PCT/US2015/022285.
International Preliminary Report on Patentability dated Aug. 20, 2018 for PCT/US2017/030117.
International Search Report and Written Opinion dated May 8, 2019 for PCT/US2019/014061.
European Supplementary Search Report dated Jul. 7, 2015 for EP 13 757 017.2.
Extended European Search Report dated Oct. 26, 2016 for EP 14 782 619.2.
Extended European Search Report dated Apr. 13, 2017 for EP 14 871 789.5.
Extended European Search Report dated Oct. 26, 2017 for EP 15 768 892.
European Examination Report dated Nov. 23, 2017 for EP 14 782 619.2.
European Search Report dated Feb. 12, 2018 for EP 14 571 789.
European Examination Report dated Nov. 6, 2018 for EP 15 768 892.0.
European Supplementary Partial Search Report dated Feb. 11, 2019 for EP 17 790 538.7.
European Summons to Attend Oral Proceedings dated Feb. 11, 2019 for EP 14 782 619.2.
Canadian Office Action dated Oct. 17, 2016 for CA 2,911,692.
Canadian Office Action dated Oct. 10, 2017 for CA 2,911,692.
Canadian Office Action dated Aug. 27, 2019 for CA 3,023,468.
Korean Office Action dated Feb. 20, 2017 for KR 10-2015-7032122 with translation.
Korean Office Action dated Aug. 25, 2017 for KR 10-2015-7032122 with translation.
Korean Office Action dated Nov. 16, 2017 for KR 10-2015-7032122 with translation.
Japanese Office Action dated Dec. 19, 2017 for JP 2016-0560872.
Taiwan Office Action dated Sep. 19, 2019 for TW106114364.
Zhu et al., "Comprehensive toxicity and immunogenicity studies reveal minimal effects in mice following sustained dosing of extracellular vesicles derived from HEK293T cells," Journal of Extracellular Vesicles, Published online Jun. 6, 2017, https://doi.org/10.1080/20013078.2017.1324730.
Au et al., "MiR-1303 Regulates Mycobacteria Induced Autophagy by Targeting Atg2B", PLOS One, 2016, vol. 11, No. 1, pp. 14.
Ghanbari et al., "Genetic Variations in MicroRNA-Binding Sites Affect MicroRNA-Mediated Regulation of Several Genes Associated with Cardio-Metabolic Phenotypes", Cardiovascular Genetics, Jun. 2015, vol. 8, pp. 473-486.

(56) References Cited

OTHER PUBLICATIONS

International Search Report and Written Opinion received in PCT Application No. PCT/US2020/023011, dated Jul. 9, 2020 in 15 pages.
Lerebours et al., "miRNA Expression Profiling of Inflammatory Breast Cancer Identifies a 5-miRNA Signature Predictive of Breast Tumor Aggressiveness", International Journal of Cancer, 2013, vol. 133, No. 7, in 11 pages.
Das et al., "Differential Expression of miRNAs by Macrophages Infected with Virulent and Avirulent Mycobacterium Tuberculosis", Tuberculosis, vol. 93, Supplement, Dec. 1, 2013, pp. S47-S50.

* cited by examiner

SEQUENCE LISTING

```
<160> NUMBER OF SEQ ID NOS: 10

<210> SEQ ID NO 1
<211> LENGTH: 23
<212> TYPE: RNA
<213> ORGANISM: Homo sapiens

<400> SEQUENCE: 1

ugugcaaauc uaugcaaaac uga                                      23


<210> SEQ ID NO 2
<211> LENGTH: 22
<212> TYPE: RNA
<213> ORGANISM: Homo sapiens

<400> SEQUENCE: 2

agcagcauuu acagggcuau ga                                       22


<210> SEQ ID NO 3
<211> LENGTH: 21
<212> TYPE: RNA
<213> ORGANISM: Homo sapiens

<400> SEQUENCE: 3

uaaagugcug acagugcaga u                                        21
```

```
<210> SEQ ID NO 4
<211> LENGTH: 15
<212> TYPE: RNA
<213> ORGANISM: Homo sapiens

<400> SEQUENCE: 4

gagaacgaac caggg                                                    15

<210> SEQ ID NO 5
<211> LENGTH: 22
<212> TYPE: RNA
<213> ORGANISM: Homo sapiens

<400> SEQUENCE: 5

cguguauuug acaagcugag uu                                            22

<210> SEQ ID NO 6
<211> LENGTH: 17
<212> TYPE: RNA
<213> ORGANISM: Homo sapiens

<400> SEQUENCE: 6

cuccgggacg gcugggc                                                  17

<210> SEQ ID NO 7
<211> LENGTH: 22
<212> TYPE: RNA
<213> ORGANISM: Homo sapiens

<400> SEQUENCE: 7

uuuagagacg gggucuugcu cu                                            22

<210> SEQ ID NO 8
<211> LENGTH: 22
<212> TYPE: RNA
<213> ORGANISM: Homo sapiens

<400> SEQUENCE: 8

gcugggauua caggcaugag cc                                            22

<210> SEQ ID NO 9
<211> LENGTH: 19
<212> TYPE: RNA
<213> ORGANISM: Homo sapiens

<400> SEQUENCE: 9

ggagauggag guugcagug                                                19

<210> SEQ ID NO 10
<211> LENGTH: 22
<212> TYPE: RNA
<213> ORGANISM: Homo sapiens

<400> SEQUENCE: 10

uaccugggag acugagguug ga                                            22
```

MICRORNA COMPOSITIONS AND METHODS OF MAKING AND USING SAME

CROSS-REFERENCE TO RELATED APPLICATIONS

This application is a non-provisional of and claims priority to U.S. Provisional Patent Application No. 62/329,486 filed Apr. 29, 2016 and entitled "Compositions for Cellular Restoration and Methods of Making and Using Same," and U.S. Provisional Patent Application No. 62/482,465 filed Apr. 6, 2017 and entitled "MicroRNA Compositions and Methods of Making and Using Same," each of which is incorporated by reference herein in its entirety.

TECHNICAL FIELD

The present disclosure generally relates to compositions and methodologies for the improvement and/or restoration of one or more aspects of cellular function. More specifically this disclosure relates to prophylactic and/or therapeutic utilization of microRNA.

BACKGROUND

Aging is an important risk factor for most chronic diseases and is the primary factor for the majority of morbidity and health care expenditures in developed nations. Decreased cellular function associated with cellular senescence results in the disorders and dysfunctions typically associated with aging mammalian cells. A potent inducer of cellular senescence is (epi)genomic stress, which can result from direct DNA damage, dysfunctional telomeres, disrupted chromatin, or strong mitogenic signals. Additionally, cellular senescence can cause chronic inflammation mediated, at least in part, by senescence-associated secretory factors.

There exists an ongoing need for compositions and methods that improve cellular functions which have been negatively impacted due to one or more mechanisms associated with cellular senescence. Further, there exists an ongoing need for compositions and methods to improve the cellular health of a subject.

SUMMARY

Disclosed herein is a method comprising administering to a subject a composition comprising an isolated microRNA having a sequence selected from the group consisting of miR-19a-3p (SEQ ID NO:1); miR-103a-3p (SEQ ID NO:2); miR-106b-5p (SEQ ID NO:3); miR-146a-5p (SEQ ID NO:4); miR-223-5p (SEQ ID NO:5); miR-4497 (SEQ ID NO:6); miR-1303 (SEQ ID NO:7); miR-619-5p (SEQ ID NO:8); miR-1273f (SEQ ID NO:9); miR-7851-3p (SEQ ID NO:10); a functional variant thereof and combinations thereof.

Also disclosed herein is a method of preparing a restored stem cell comprising i) obtaining a sample comprising adult stem cells; ii) culturing the sample in the presence of an isolated microRNA having a sequence selected from the group consisting of miR-19a-3p (SEQ ID NO:1); miR-103a-3p (SEQ ID NO:2); miR-106b-5p (SEQ ID NO:3); miR-146a-5p (SEQ ID NO:4); miR-223-5p (SEQ ID NO:5); miR-4497 (SEQ ID NO:6); miR-1303 (SEQ ID NO:7); miR-619-5p (SEQ ID NO:8); miR-1273f (SEQ ID NO:9); miR-7851-3p (SEQ ID NO:10); a functional variant thereof; and combinations thereof to produce the restored stem cells;

and iii) recovering the restored stem cells from the sample wherein the restored stem cells when compared to the adult stem cells are characterized by a change in expression of greater than about 1.5 fold for one or more genes selected from the group consisting of C-abl oncogene-1 non-receptor tyrosine kinase; V-akt murine thymona viral oncogene homolog 1; aldehyde dehydrogenase 1 family, member A3; Ataxia telangiectasia mutated; BMI1 polycomb ring finger oncogene; calrecticulin; cyclin A2; cyclin B1; cyclin D1; cyclin E1; CD44 molecule, cell division cycle 25 homolog C; cyclin-dependent kinase 2; cyclin-dependent kinase 4; cyclin-dependent kinase 6; cyclin-dependent kinase inhibitor 1A; cyclin-dependent kinase inhibitor 1B; cyclin-dependent kinase inhibitor 1C; cyclin-dependent kinase inhibitor 2A; cyclin-dependent kinase inhibitor 2B; cyclin-dependent kinase inhibitor 2C; and cyclin-dependent kinase inhibitor 2D.

Also disclosed herein is a method of preparing a restored stem cell composition comprising (i) obtaining a cell sample comprising adult stem cells; (ii) introducing a vector construct containing a nucleic acid sequence for expression of an isolated microRNA having a sequence selected from the group consisting of miR-19a-3p (SEQ ID NO:1); miR-103a-3p (SEQ ID NO:2); miR-106b-5p (SEQ ID NO:3); miR-146a-5p (SEQ ID NO:4); miR-223-5p (SEQ ID NO:5); miR-4497 (SEQ ID NO:6); miR-1303 (SEQ ID NO:7); miR-619-5p (SEQ ID NO:8); miR-1273f (SEQ ID NO:9); miR-7851-3p (SEQ ID NO:10); a functional variant thereof; and combinations thereof into the adult stem cells to produce restored stem cells; and (iii) recovering the restored stem cells.

Also disclosed herein is a pharmaceutical formulation comprising an adult stem cell wherein the adult stem cell comprises a plasmid containing a promoter element operably linked to an oligonucleotide for expression of a microRNA having a sequence selected from the group consisting of miR-19a-3p (SEQ ID NO:1); miR-103a-3p (SEQ ID NO:2); miR-106b-5p (SEQ ID NO:3); miR-146a-5p (SEQ ID NO:4); miR-223-5p (SEQ ID NO:5); miR-4497 (SEQ ID NO:6); miR-1303 (SEQ ID NO:7); miR-619-5p (SEQ ID NO:8); miR-1273f (SEQ ID NO:9); miR-7851-3p (SEQ ID NO:10); a functional variant thereof; and combinations thereof.

Also disclosed herein is a pharmaceutical formulation comprising an isolated microRNA selected from the group consisting of miR-19a-3p (SEQ ID NO:1); miR-103a-3p (SEQ ID NO:2); miR-106b-5p (SEQ ID NO:3); miR-146a-5p (SEQ ID NO:4); miR-223-5p (SEQ ID NO:5); miR-4497 (SEQ ID NO:6); miR-1303 (SEQ ID NO:7); miR-619-5p (SEQ ID NO:8); miR-1273f (SEQ ID NO:9); miR-7851-3p (SEQ ID NO:10); a functional variant thereof; and combinations thereof.

DETAILED DESCRIPTION

Figure 1:
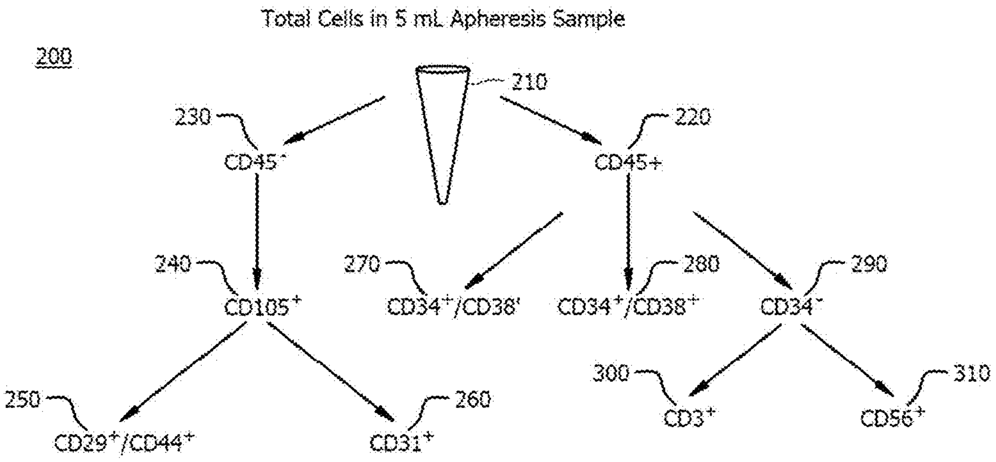
FIG. 1 is a depiction of an aspect of immunophenotyping a cell sample.

Disclosed herein are methods of increasing the amount of microRNAs of the type described herein either locally or systemically in a subject. For example, a method of the present disclosure may comprise administering to a subject, a composition comprising one or more microRNAs of the type disclosed herein. In another aspect, the present disclosure contemplates a method comprising introducing into a subject cells that have been altered to express elevated amounts of the microRNAs disclosed herein. In yet another aspect of the present disclosure, a method comprises administering to a subject a microvesicle (e.g., exosome) modified to contain elevated amounts of a microRNA of the type disclosed herein. In an aspect, at least part of the membrane of the microvesicle is directly obtained from a cell. Alternatively, the microvesicle is synthetic.

In yet other aspects of the present disclosure, a method comprises administering to a subject cells transformed with a plasmid vector that provides inducible or constitutive expression of a microRNA of the type disclosed herein. Such methods may be therapeutic and result in the treatment of one or more adverse medical conditions the subject is experiencing. In the alternative such methods may be prophylactic in nature.

In order for the present disclosure to be more readily understood, certain terms are first defined below. Additional definitions for the following terms and other terms are set forth throughout the specification.

microRNA: As used herein, the term "microRNAs (miRNAs)" refers to post-transcriptional regulators that typically bind to complementary sequences in the three prime untranslated regions (3' UTRs) of target messenger RNA transcripts (mRNAs), usually resulting in gene silencing. Typically, miRNAs are short ribonucleic acid (RNA) molecules, for example, 21 or 22 nucleotides long or less. The terms "microRNA" and "miRNA" are used interchangeably.

microRNA mimic: As used herein refers to synthetic non-coding RNAs that are capable of entering the RNAi pathway and regulating gene expression. As used herein, "synthetic microRNA" refers to any type of RNA sequence, other than endogenous microRNA. microRNA mimics imitate the function of endogeneous microRNAs and can be designed as mature, double-stranded molecules or mimic precursors (e.g., pri- or pre-microRNAs). MicroRNA mimics can be comprised of modified or unmodified RNA, DNA, RNA-DNA hybrids or alternative nucleic acid chemistries.

Microvesicle: As used herein, the term "microvesicle" refers to a membranaceus particle comprising fragments of plasma membrane derived from various cell types. Typically, microvesicles have a diameter (or largest dimension where the particle is not spheroid) of between about 10 nm to about 5000 nm (e.g., between about 50 nm and 1500 nm, between about 75 nm and 1500 nm, between about 75 nm and 1250 nm, between about 50 nm and 1250 nm, between about 30 nm and 1000 nm, between about 50 nm and 1000 nm, between about 100 nm and 1000 nm, between about 50 nm and 750 nm, etc.). Microvesicles suitable for use in the present invention may originate from cells by membrane inversion, exocytosis, shedding, blebbing, and/or budding. Depending on the manner of generation (e.g., membrane inversion, exocytosis, shedding, or budding), the microvesicles contemplated herein may exhibit different surface/lipid characteristics. Alternative names for microvesicles include, but are not limited to, exosomes, ectosomses, membrane particles, exosome-like particles, and apoptotic vesicles.

Subject: As used herein, the term "subject" refers to a human or any non-human animal (e.g., mouse, rat, rabbit, dog, cat, cattle, swine, sheep, horse or primate). A human includes pre and post-natal forms. In many aspects, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Treatment: As used herein is a clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition. "Treatments" refer to one or both of therapeutic treatment and prophylactic or preventative measures. Those in need of treatment include those already affected by a disease or disorder or undesired physiological condition as well as those in which the disease or disorder or undesired physiological condition is to be prevented.

Effective amount: As used herein refers to an amount sufficient to effect beneficial or desirable biological and/or clinical results.

Expression vector: As used herein is a nucleic acid construct, generated recombinantly or synthetically, bearing a series of specified nucleic acid elements that enable transcription of a particular gene in a host cell. Typically, gene expression is placed under the control of certain regulatory elements, such as constitutive or inducible promoters.

Operably linked: As used herein is used to describe the connection between regulatory elements and a gene or its coding region. That is, gene expression is typically placed under the control of certain regulatory elements, for example, without limitation, constitutive or inducible promoters, tissue-specific regulatory elements, and enhancers. A gene or coding region is said to be "operably linked to" or "operatively linked to" or "operably associated with" the regulatory elements, meaning that the gene or coding region is controlled or influenced by the regulatory element.

Pharmaceutically acceptable: As used herein refers to carriers, excipients, or stabilizers that are nontoxic to the cell or mammal being exposed thereto at the dosages and concentrations employed or that have an acceptable level of toxicity as determined by the skilled practitioner. A nonlimiting example of a physiologically acceptable carrier is an aqueous pH buffered solution. The physiologically acceptable carrier may also comprise one or more of the following: antioxidants, such as ascorbic acid, low molecular weight (less than about 10 residues) polypeptides, proteins, such as serum albumin, gelatin, immunoglobulins, hydrophilic polymers such as polyvinylpyrrolidone, amino acids, carbohydrates such as glucose, mannose, or dextrins, chelating agents such as EDTA, sugar alcohols such as mannitol or sorbitol, salt-forming counterions such as sodium, and nonionic surfactants such as Tween™, polyethylene glycol (PEG), and Pluronics™.

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from at least about 10%, about 20%, about 30%, about 40%, about 50%, about 60%, about 70%, about 80%, about 90%, about 95%, about 98%, about 99%, substantially 100%, or 100% of the other components with which they were initially associated. In some aspects, isolated agents are more than about 80%, about 85%, about 90%, about 91%, about 92%, about 93%, about 94%, about 95%, about 96%, about 97%, about 98%, about 99%, substantially 100%, or 100% pure. As used herein, a substance is "pure" if it is substantially free of other components. As used herein, the term "isolated cell" refers to a cell not contained in a multi-cellular organism.

In an aspect, a composition for use in the present disclosure comprises one or more microRNAs selected from the group consisting of miR-19a-3p (SEQ ID NO:1); miR-103a-3p (SEQ ID NO:2); miR-106b-5p (SEQ ID NO:3); miR-146a-5p (SEQ ID NO:4); miR-223-5p (SEQ ID NO:5); miR-4497 (SEQ ID NO:6); miR-1303 (SEQ ID NO:7); miR-619-5p (SEQ ID NO:8); miR-1273f (SEQ ID NO:9); miR-7851-3p (SEQ ID NO:10); a functional variant thereof; and combinations thereof. As used herein, the term "functional variant" of a microRNA sequence refers to an oligonucleotide sequence that varies from the natural microRNA sequence, but retains one or more functional characteristics of the microRNA (e.g., specific microRNA target inhibition). In some aspects, a functional variant of a microRNA sequence retains all of the functional characteristics of the microRNA. In certain aspects, a functional variant of a microRNA has a nucleobase sequence that is a least about 60%, 65%, 70%, 75%, 80%, 85%, 90%, 91%, 92%, 93%, 94%, 95%, 96%, 97%, 98% or 99% identical to the microRNA or precursor thereof over a region of about 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleobases, or that the functional variant hybridizes to the complement of the microRNA or precursor thereof under stringent hybridization conditions. Accordingly, in certain aspects the nucleobase sequence of a functional variant may be capable of hybridizing to one or more target sequences of the microRNA.

In some aspects, a functional variant of a microRNA disclosed herein comprises at least about 65%, 70%, 75%, 80%, 85%, 90%, 91%, 92%, 93%, 94%, 95%, 96%, 97%, 98% or 99% identical sequence identity with SEQ ID NO:1; alternatively at least 65%, 70%, 75%, 80%, 85%, 90%, 91%, 92%, 93%, 94%, 95%, 96%, 97%, 98% or 99% sequence identity with SEQ ID NO:2; alternatively at least 65%, 70%, 75%, 80%, 85%, 90%, 91%, 92%, 93%, 94%, 95%, 96%, 97%, 98% or 99% sequence identity with SEQ ID NO:3; alternatively at least 65%, 70%, 75%, 80%, 85%, 90%, 91%, 92%, 93%, 94%, 95%, 96%, 97%, 98% or 99% sequence identity with SEQ ID NO:4; alternatively at least 65%, 70%, 75%, 80%, 85%, 90%, 91%, 92%, 93%, 94%, 95%, 96%, 97%, 98% or 99% sequence identity with SEQ ID NO:5; alternatively at least 65%, 70%, 75%, 80%, 85%, 90%, 91%, 92%, 93%, 94%, 95%, 96%, 97%, 98% or 99% sequence identity with SEQ ID NO:6; alternatively at least 65%, 70%, 75%, 80%, 85%, 90%, 91%, 92%, 93%, 94%, 95%, 96%, 97%, 98% or 99% sequence identity with SEQ ID NO:7; alternatively at least 65%, 70%, 75%, 80%, 85%, 90%, 91%, 92%, 93%, 94%, 95%, 96%, 97%, 98% or 99% sequence identity with SEQ ID NO:8; alternatively at least 65%, 70%, 75%, 80%, 85%, 90%, 91%, 92%, 93%, 94%, 95%, 96%, 97%, 98% or 99% sequence identity with SEQ ID NO:9; or alternatively at least 65%, 70%, 75%, 80%, 85%, 90%, 91%, 92%, 93%, 94%, 95%, 96%, 97%, 98% or 99% sequence identity with SEQ ID NO:10.

In some aspects, a functional variant of a microRNA disclosed herein comprises from 65% to about 99% sequence identity with SEQ ID NO:1; alternatively from 65% to about 99% sequence identity with SEQ ID NO:2; alternatively from 65% to about 99% sequence identity with SEQ ID NO:3; alternatively from 65% to about 99% sequence identity with SEQ ID NO:4; alternatively from 65% to about 99% sequence identity with SEQ ID NO:5; alternatively from 65% to about 99% sequence identity with SEQ ID NO:6; alternatively from 65% to about 99% sequence identity with SEQ ID NO:7; alternatively from 65% to about 99% sequence identity with SEQ ID NO:8; alternatively from 65% to about 99% sequence identity with SEQ ID NO:9; or alternatively from 65% to about 99% sequence identity with SEQ ID NO:10.

In an aspect, any of the microRNAs disclosed herein when utilized is an isolated molecule that is substantially pure. Herein substantially pure refers to the microRNA when it is at least 10%, 20%, 30%, 40%, 50%, 60%, 70%, 75%, 80%, 85%, or over 90%, 95%, or 99% by weight, of the total material in a sample. Thus, for example, a microRNA molecule that is chemically synthesized, produced by recombinant technology, or isolated by known purification techniques, will be generally be substantially free from its naturally associated components. A substantially pure microRNA molecule therefore can be obtained, for example, by extraction from a natural source; by expression of a recombinant nucleic acid molecule encoding the microRNA molecule; or by chemical synthesis.

In an aspect, a first method of the present disclosure comprises (i) obtaining stem cells from a subject; and (ii) associating the obtained stem cells with microRNAs of the type disclosed herein to form restored cells. A method of the present disclosure may further comprise introducing the restored cells to a subject.

In an aspect of the present disclosure, stem cells are obtained from a subject. In some aspects, the subject is identified as having one or more risk factors associated with the development of an adverse medical condition. In yet another aspect, the subject has not been diagnosed with a medical condition and/or has not been identified as having one or more risk factors associated with the development of a medical condition. It is contemplated that the methodologies disclosed herein may be employed in the treatment of subjects having a medical condition for which additional therapies have been previously or are currently being employed. It is further contemplated that in an aspect, a subject has undergone or is currently undergoing one or more therapies for medical conditions not associated with the medical condition for which the subject will be treated using the compositions and methodologies disclosed herein. In an aspect, the subject has one or more age-related medical conditions.

In an aspect of the present aspect, the subject is administered an effective amount of a mobilizer. Herein a "mobilizer" or a "mobilizer of hematopoietic stem cells or progenitor cells" (used interchangeably) refers to any substance, whether it is a synthetic, small organic molecule, naturally-derived small organic molecule, a polypeptide, such as a growth factor or colony-stimulating factor or an active fragment or mimic thereof, a nucleic acid, a carbohydrate, an antibody, or any other agent that acts to enhance the migration of stem cells from the bone marrow into the peripheral blood. Such a "mobilizer" may increase the number of stem cells (e.g., hematopoietic stem cells or hematopoietic progenitor/precursor cells) in the peripheral blood, thus allowing for a more accessible source of stem cells for use in the methods disclosed herein. Any mobilizer suitable for increasing the number of stem cells in the subject that are available to be harvested and is compatible with the other aspects of this disclosure may be utilized. In an aspect, the mobilizer is a cytokine such as granulocyte colony-stimulating factor (G-CSF). A commercial example of a mobilizer suitable for use in the present disclosure is NEUPOGEN® (filgrastim) which is a prescription medication used to treat neutropenia that is commercially available from Amgen. Another example of a mobilizer suitable for use in the present disclosure is a recombinant methionyl human stem cell factor which is commercially available as STEMGEN® from Amgen. Yet another example of a mobilizer suitable for use in the present disclosure is PLERIXAFOR which is an inhibitor of the CXCR4 chemokine receptor and blocks binding of its cognate ligand, stromal cell-derived factor-1α (SCF-1α) and is commercially available as MOZOBIL® from Genzyme.

An effective amount of a mobilizer may be determined by the ordinarily skilled artisan consistent with best medical practices and taking into account a variety of factors including, for example and without limitation, the subject's general health and body mass.

Subsequent to administration of the mobilizer, and after a suitable time period has elapsed; a cell sample may be harvested from a subject. The time period between administration of the mobilizer to the subject and harvesting of the cell sample may be varied to meet one or more user and/or process goals. In an aspect, the time period between administration of the mobilizer and harvesting of the cell sample may range from about 24 hours to about 10 days, alternatively from about 48 hours to about 7 days, or alternatively from about 3 days to about 5 days.

As known to one of ordinary skill in the art, stem cells have been identified in various organs and tissues, including brain, bone marrow, peripheral blood, blood vessels, skeletal muscle, skin, teeth, heart, gut, liver, ovarian epithelium, and testis. It is within the scope of this disclosure to conduct various aspects of the present methods using cell samples comprising stem cells obtained from any of the tissues known to be a source of stem cells. Thus the present disclosure in one aspect contemplates the isolation of stem cells from any tissue using a methodology appropriate to that source of stem cells. Consequently, in some aspects, a methodology of the present disclosure comprises obtaining stem cells from a subject who has not been administered a mobilizer of the type disclosed herein.

In an aspect, the cell sample is harvested from a subject using any suitable methodology, for example, using an extracorporeal therapy such as apheresis. Apheresis is a method used to collect only a specific part of the subject's blood. It works on the basis of centrifugation or rapid spinning of the blood. A pathway is established for the subject's blood and allows for connection to the apheresis device. The instrument uses small pumps to move blood and fluids through the system. One pump draws blood out of one arm or side of the catheter and directs it to the centrifuge where the blood is separated into red cell, white cell, and plasma layers. A portion of the white cell layer, which includes stem cells, and a small amount of plasma and red cells are diverted to a collection bag. The rest of the blood is returned to the subject in the other arm or the second side of the catheter. In such an aspect, the cell sample is harvested using intravenous needles located in a vein in each arm of a subject. Blood may be removed from a first vein, passed through an extracorporeal circuit that separates out the cell sample of interest and the remaining material may be returned to a second vein.

In an aspect, the cell sample is harvested from the bone marrow directly. For example, the cell sample may be harvested from the iliac crest of a subject. In such aspects, bone marrow aspiration to obtain the cell sample may involve a healthcare provider locating the posterior iliac crest of the subject subsequent to carrying out standard precautions such as skin sterilization and the administration of a local anesthetic. A suitable needle with the stylet in place may be slowly advanced through the skin and subcutaneous tissue pointing towards the anterior superior iliac spine. Upon reaching the posterior iliac crest, the area may be penetrated by the needle until an adequate depth is reached. Once the needle is in place, the stylet may be removed, a syringe attached, and the aspiration performed.

In an aspect, a plurality of stem cell collections (e.g., bone marrow aspirations) is carried out in order to obtain some user and/or process desired number of cells in the cell sample. For example, the number of cells collected may range from $1\times10^6$-$1.0\times10^9$ cells/kg of the subject weight, alternatively from about $2\times10^6$-$1.0\times10^8$ cells/kg of the subject weight, or alternatively from about $5\times10^6$-$1.0\times10^8$ cells/kg of the subject weight. Cell samples harvested as disclosed herein may be utilized without further processing in the methodologies disclosed herein. Alternatively, cell samples harvested as disclosed herein may be further processed using any methodology compatible with the compositions and methodologies disclosed herein. Alternatively, cell samples harvested as disclosed herein may be stored for some time period before being utilized in the methodologies and therapies disclosed herein. Storage of the cell samples may involve, for example, cryogenic preservation of the cell sample in a biocompatible solution to stabilize the sample for the duration of storage. "Biocompatible solution" refers to solutions in which the cell samples are suspended for use in the cellular restoration methodologies disclosed herein or for any other subsequent uses. Such biocompatible solutions may include saline and may further comprise other ingredients such as preservatives, antimicrobials, and the like.

In an aspect, the cell samples comprise adult stem cells and/or adult stem cell material which refer to stem cells or stem cell material that are not embryonic in origin nor derived from embryos or fetal tissue. In an aspect, the cell samples comprise stem cells and/or stem cell material that are embryonic in origin and/or derived from embryos or fetal tissue.

In an aspect, cell samples harvested as disclosed herein are stored for greater than about 24 hours prior to being utilized in the methodologies disclosed herein. Alternatively, the cell samples harvested as disclosed herein are stored for a period of time ranging from about 1 hour to about 20 years prior to being utilized in the methodologies disclosed herein. Alternatively, storage of a cell sample harvested as disclosed herein may be for a time period ranging from about 10 days to about 15 years, alternatively from about 30 days to about 10 years, or alternatively from about 30 days to about 5 years.

As will be understood by the ordinarily skilled artisan, the cell sample, as harvested, comprises a heterogeneous cell population. An aspect of the methodologies disclosed herein comprises identifying and quantifying the number and types of cells present in the cell sample. Any methodology suitable for characterizing the number and types of cells present in the cell sample may be employed. In an aspect, the cell sample is characterized by immunophenotyping. Herein, immunophenotyping refers to the analysis of heterogeneous populations of cells for the purpose of identifying the presence and proportions of the various populations in the sample. Antibodies are used to identify cells by detecting specific antigens (termed markers) expressed by these cells. In an aspect, the cell samples are characterized by immunophenotyping using techniques such as flow cytometry. In alternative aspects, characterizations of the various cell types present in a cell sample may be carried out using any suitable methodology such as reverse transcriptase polymerase chain reaction (RT-PCR) or immunocytochemistry.

In an aspect, the populations of cells or cell types present in the cell sample are identified based on the presence or absence of one or more cell surface markers. An aspect of a flow cytometry protocol for the identification of the different populations of cells (e.g., cell types) in a cell sample, 200, is presented in FIG. 1. Referring to FIG. 1, a cell sample 210 is subjected to flow cytometry. In an aspect, the sample 210 may be, at a first stage, sorted into hematopoietic cells 220 and non-hematopoietic cells 230 based on the presence or absence of CD45. CD45, also known as leukocyte common antigen (LCA), T200, B220, LyS, and protein tyrosine phosphatase receptor type C (PTPRC) is a transmembrane glycoprotein of the leukocyte-specific-receptor-like protein tyrosine phosphatase family. It is expressed on all nucleated hematopoietic cells and can cover up to 10% of the cell surface area. CD45 functions as a regulator of T-cell and B-cell antigen receptor signaling and is a regulator of cell growth and cell differentiation.

In an aspect, CD45− cells, identified as non-hematopoietic stem cells 230, may be further characterized on the basis of the presence or absence of CD105. CD105, also known as endoglin, HHT1, ORW, and SH-1 is a type I membrane glycoprotein located on cell surfaces and is a component of the TGFβ receptor complex. CD105 may play a role in hematopoiesis and angiogenesis. In an aspect, a cell population that is both CD45− and CD105+, 240, is characterized as having both mesenchymal stem cells and endothelial progenitor cells.

In an aspect, a cell population that is identified to be both CD45− and CD105+, 240, may be further sorted into mesenchymal stem cells and endothelial progenitor cells. In an aspect, the mesenchymal stem cells are identified as being CD45−, CD105+, CD29+ and CD44+, 250. CD29, also known as platelet GPIIa, integrin β1 and GP is an integrin unit associated with very late antigen receptors and functions in cell adhesion. CD44, also known as ECMRII, H-CAM, Pgp-1, HUTCH-1, Hermes antigen, phagocytic glycoprotein I, extracellular matrix receptor III, GP90 lymphocyte homing/adhesion receptor, and hyaluronate receptor functions in cell adhesion and migration. In an aspect, endothelial progenitor cells are identified as being CD45−, CD105+, and CD31+, 260. CD31, also known as PECAM-1, endoCAM, platelet endothelial cell adhesion molecule, and PECA-1 is a protein that in humans is encoded by the PECAM1 gene found on chromosome 17. CD31 is thought to function in cell adhesion, activation, and migration.

The method of the present disclosure may further comprise identifying the differing hematopoietic cell types present in the CD45+ cells, 220. In an aspect, a population of the cells is identified as being primitive hematopoietic stem cells, 270, on the basis of being CD45+, CD34+ and CD38−. In an aspect, a population of the cells is identified as being hematopoietic progenitor cells on the basis of being CD45+, CD34+ and CD38+, 280. CD34 also known as gp105-120 and hematopoietic progenitor cell antigen (HPCA-1) is a member of the family of single-pass transmembrane sialomucin proteins that are expressed on early hematopoietic and vascular tissues. CD34 is thought to function in cell adhesion. CD38, also known as ADP-ribosyl cyclase, T10, and cyclic ADP-ribose hydrolase 1 is a multifunctional ectonucleotidase encoded by the CD38 gene which is located on chromosome 4. In an aspect, at least a portion of the cell population are CD45+ and CD34−, 290, and are identified as differentiated hematopoietic cells. In such an aspect, the differentiated hematopoietic cells, 290, may be further defined as being T-lymphocytes, 300, or Natural Killer cells, 310. T-lymphocytes can be characterized as being CD45+, CD34−, and CD3+. CD3, also known as T3, is a protein complex and plays a role in cell adhesion between T-cells and other cell types. Natural Killer cells can be characterized as being CD45+, CD34−, and CD56+. CD56 also known as Leu-19, NKH-1, and neural cell adhesion molecule (NCAM) is a hemophilic binding glycoprotein that may function in cell-cell adhesion, neurite outgrowth, synaptic plasticity, and learning and memory.

In an aspect, the cell sample may be characterized using the methodologies disclosed herein. Such characterizations may result in the identification of cell populations in the cell sample that include without limitation, non-hematopoietic cells, mesenchymal stem cells, endothelial progenitor cells, hematopoietic cells, primitive hematopoietic stem cells, hematopoietic progenitor cells, differentiated hematopoietic cells, T-lymphocytes, natural killer cells, or combinations thereof. It is contemplated that the surface markers described herein represent one methodology for the identification of cell populations present within the cell sample. As will be understood by the ordinarily skilled artisan, numerous markers and combination of markers other than those disclosed herein may be utilized to identify and characterize the cell populations present within the cell sample. Further, the identification of the various cell populations present in the cell sample may be carried out to the extent described herein, may include determination of the presence or absence of additional surface markers, may utilize fewer markers than disclosed herein, or may be carried out to a lesser extent such that fewer populations of cells within the cell sample are identified. In an aspect, a method comprises excluding the identification of the different populations of cells present in a cell sample.

In an aspect, a cell sample may be further characterized based on the number of senescent cells and non-senescent cells present in the cell sample. Herein, non-senescent cells refer to the cells that retain the ability to divide many times over without showing replicative senescence. Herein senescent cells refer to cells having a long-term loss of proliferative capacity despite continued viability and metabolic activity.

Senescent cells may be identified using a variety of metrics that include for example loss of proliferation, morphological changes, decreased telomere lengths, increased S-β-GAL activity, the production of senescence-associated heterochromatic foci (SAHF), increased production of senescence-associated secretory factors (SASF), increased production of reactive oxygen species (ROS), increased DNA damage, decreased chaperone-mediated autophagy, or combinations thereof. It is contemplated that changes in the various metrics described are assessed relative to comparable cell types established to be non-senescent cells. Alternatively, the characteristics of the cell sample may be compared to literature values established for the analyzed metric in a corresponding non-senescent cell.

Non-senescent cells may characterized by the length of their telomeres and of the level of telomerase activity present in the cell. By way of a non-limiting example, non-senescent cells present in the cell sample may be characterized by telomere lengths greater than or equal to about 4 kilobases, alternatively 4.5 kilobases, or alternatively 5 kilobases. It will be understood by the ordinarily skilled artisan that teleomere lengths indicative of non-senescent cells may vary depending on the cell type. Consequently, for a particular cell type, the telomere length characteristic of a non-senescent cell may be determined by routine experimentation.

In an aspect, a cell sample of the type disclosed herein comprises greater than 90% non-senescent cells, alternatively greater than 91% non-senescent cells, alternatively greater than 92% non-senescent cells, alternatively greater than 93% non-senescent cells, alternatively greater than 94% non-senescent cells, alternatively greater than 95% non-senescent cells, alternatively greater than 96% non-senescent cells, alternatively greater than 97% non-senescent cells, alternatively greater than 98% non-senescent cells, or alternatively greater than 99% non-senescent cells. The percentage of non-senescent cells is based on the total number of cells present in the sample. In an aspect, a cell sample comprise from about 90% non-senescent cells to about 99% non-senescent cells based on the total number of cells present in the sample.

In some aspects, the non-senescent cells present in the cell sample may be identified using any suitable methodology. In such aspects, the non-senescent cells may be separated from the senescent cells using any suitable process compatible with the present disclosure to result in a cell sample that comprises, consists essentially of, or consists of non-senescent cells. It is contemplated that such methodologies may be extended to further define a population of non-senescent cells having the presence or absence of particular cell surface markers and result in a cell sample comprising, consisting essentially of, or consisting of non-senescent cells of a particular type (e.g., non-senescent mesenchymal stem cells, non-senescent natural killer cells).

In an aspect, the cell sample may be analyzed for the extent of expression of one or more genes and/or proteins associated with cellular senescence. Such analyses may be carried out using a restoration biomarker protein panel (RBPP) and/or restoration biomarker gene expression panel (RBGEP) of the types disclosed herein.

In an aspect, the RBPP comprises a plurality of antibody probes for factors linked to cellular aging and senescence. For example, the RBPP may comprise greater than 5 antibody probes, alternatively greater than 10 antibody probes, or alternatively greater than 20 antibody probes. In an aspect the RBPP comprises from 10 to 15 antibody probes. An example of a RBPP suitable for use in this disclosure is a protein array panel designated RBPP-X1 comprising one or more antibody probes to the proteins listed in Table 1:

TABLE 1

| Name | Also Known As | Designated |
|---|---|---|
| granulocyte-colony stimulating factor | colony-stimulating factor 3 | G-CSF |
| chemokine ligand 26 | eotaxin-3, macrophage inflammatory protein 4-alpha, thymic stroma chemokine, and IMAC | CCL26 |
| hepatocyte growth factor | hepatocyte scatter factor (HSF), | HGF |
| insulin-like growth factor binding protein 1 | placental protein 12 (PP12) | IGFBP-1 |
| insulin-like growth factor binding protein 4 | | IGFBP-4 |
| insulin-like growth factor binding protein 6 | | IGFBP-6 |
| insulin-like growth factor beta | catabolin | IL-β |
| macrophage inflammatory protein 3 (MIP3A) | chemokine ligand 20, liver activation regulated chemokine (LARC) | MIP-3α |

TABLE 1-continued

| Name | Also Known As | Designated |
|---|---|---|
| stem cell factor | KIT-ligand, KL, steel factor | SCF |
| thymus and activation regulated chemokine | chemokine ligand 17 (CCL17), | TARC |
| transforming growth factor beta 1 | | TGF-β1 |
| tumor necrosis factor receptor superfamily member 1A | | sTNFR1 |
| vascular endothelial growth factor | | VEGF |

In an aspect, the RBGEP may comprise greater than 5 gene probes, alternatively greater than 10 gene probes, or alternatively, greater than 20 gene probes. In an aspect, the RBGEP comprises from 10 to 15 gene probes. In some aspects, the RBGEP comprises gene probes for factors linked to the regulation of cell cycle or the p53 pathway such as IFBP3, CSC25C, ABL1, CDKN2B, ALDH1A3, SIRT1, ING1, CITED2, CDKN1C, or combinations thereof. The RBGEP may further comprise gene probes for factors associated with regulation of inflammatory processes such as CDKN1A, IRF3, EGR1, IFNG, CDKN1B, NFKB1, SERPING2, IGFBP7, IRF7 or combinations thereof. The RBGEP may further comprise gene probes for factors associated with regulation of DNA damage related-processes such as PCNA, TERT, TP53BP1 or combinations thereof. The RBGEP may further comprise gene probes for factors associated with oxidative stress such as PRKCD, SOD1, NOX4 or combinations thereof. The RBGEP may further comprise gene probes for factors associated with cellular senescence such as CDKN2A, CDK6, TWIST, ATM, CCND1, ETS2, RBL2, BMI1, ETS1 or combinations thereof. The RBGEP may further comprise gene probes for factors associated with the MAPK pathway such as HRAS, MAP2K3 or combinations thereof. The RBGEP may further comprise gene probes for factors associated with cytoskeletal function such as VIM, PIK3CA, THBS1 or combinations thereof. The RBGEP may further comprise gene probes for factors associated with the p16 effector pathway such as TBX3, TBX2 or combinations thereof. The RBGEP may further comprise gene probes for factors associated with insulin signaling such as IGFBP5. The RBGEP may further comprise gene probes for factors associated with cell adhesion such as CDL3A1, CD44, TGFB1A, CDL1A1, TGFB1 or combinations thereof. The RBGEP may further comprise gene probes for factors associated with the p53 effector pathway such as E2F1, MYC or combinations thereof. An example of a RBGEP suitable for use in this disclosure, designated RBGEP-X1, is a gene panel comprising cDNA to one or more the proteins listed in Table 2:

TABLE 2

| Gene | Protein Encoded |
|---|---|
| IGFBP3 | insulin-like growth factor binding protein 3 |
| HRAS | Transforming protein p21 |
| PRKCD | protein kinase C delta |
| AKT1 | alpha serine/threonine protein kinase |
| CHEK2 | checkpoint kinase 2 |
| MAPK14 | mitogen-activated protein kinase 14 |
| IGF1 | insulin-like growth factor |
| TWIST1 | Twist-related protein 1 |
| CDC25C | M-phase inducer phosphatase 3 |
| CCNA2 | cyclin-A2 |

TABLE 2-continued

| Gene | Protein Encoded |
|---|---|
| CDK5 | cell-division protein kinase 6 |
| CCNE1 | G1/S-specific cyclin E1 |
| CHEK1 | checkpoint kinase 1 |

In an aspect, at least a portion of the cell sample are subjected to protein array analyses utilizing the RBPP-X1 array, gene expression analysis using the RBGEP-X1 array, or both. In alternative aspects, at least a portion of the cell sample are subjected to protein array analyses, gene expression analyses or both utilizing any suitable protein and/or gene array.

In an aspect, the cell sample is subjected to at least one analytical technique to characterize the quality of the cell sample. Herein, the "quality" of the cell sample refers to factors used to characterize the cellular health of the sample and includes parameters such as the number and types of cells present in the sample; the ratio of senescent to non-senescent cells in the sample; the extent of expression of a group of genetic and/or protein biomarkers; the average telomere length of the cells in the sample; the status of the innate immune function of the cells in the sample or combinations thereof. Telomere length may be determined using any suitable methodology, for example, terminal restriction fragment (TRF) analysis. Innate immune function may be evaluated using any suitable methodology such as the $^{51}Cr$ cytotoxicity release natural killer cell assay. The cell sample quality may be an assessment of the ability of the cells in the sample to improve and/or restore one or more cellular functions of the cells in the cell sample. The cell sample quality may be an assessment of the ability of the cells in the sample to exhibit improvement and/or the restoration of one or more cellular functions when subjected to the compositions and methodologies disclosed herein.

The cell sample quality may be assigned a numerical value that ranges from 1 to 10 wherein a sample having restorable or improvable cellular function has a value of 10, and a sample whose cellular function cannot be significantly improved and/or restored has a value of 1. For example, each of the following factors may weigh positively in characterization of the quality of a cell sample: relatively long telomere length; moderate level of expression of senescence-promoting genes and/or proteins; and the presence of greater than about 90% non-senescent cells. Receiver cell samples displaying these characteristics may be given a sample quality value of 10.

Utilizing the quality metrics disclosed herein (e.g., telomere length, percentage of non-senescent cells), an aspect of the present disclosure comprises evaluating the quality of the cell sample and identifying samples suitable for use in the disclosed methodologies. For example, a cell sample having a quality value of less than 3 may be deemed unsuitable for use in the presently disclosed methodologies. It is to be understood that the quality values may be assigned based on any number of metrics used to assess the quality of a cell sample. Consequently, based on the parameters used to make the assignment of a quality value, the characteristics associated with a particular quality value may differ.

In some aspects, the cell sample having been subjected to one or more of the qualitative and quantitative characterizations described herein are further processed to provide some user and/or process desired sample containing a predetermined type and number of cells.

In an aspect, a method of the present disclosure further comprises associating the stem cells obtained from a subject with microRNAs of the type disclosed herein. For example, the obtaine stem cells may be cultured in the presence of the microRNAs of the type disclosed herein using an amount of microRNA ranging from about 1 nM to about 1000 nM, alternatively from about 10 nM to about 500 nM or alternatively from about 30 nM to about 300 nM. For example, the obtained stem cells may be cultured in appropriate media for a time period ranging from about 24 hours to about 6 weeks, alternatively, from about 1 week to about 5 weeks or alternatively, from about 2 weeks to about 4 weeks in the presence of a microRNA of the type disclosed herein. Herein, the culture media, also known as the growth media, refers to a liquid or gel containing the appropriate nutrients to support the growth of cells. Suitable culture media may be chosen by the ordinarily skilled artisan with the benefits of the present disclosure. Culturing of the obtained stem cells can be carried out under standard tissue culture conditions such as RPMI-1640 (Sigma) with 10% Fetal Bovine Serum (Sigma) or STEMSPAN ACF (Stem Cell Technologies).

In an alternative aspect, a method of the present disclosure comprises introducing to the stem cells a vector capable of inducible or constitutive expression of one or more microRNAs of the type disclosed herein. For example, an expressible form of the microRNA may be located on a vector such as a plasmid, cosmid, phagemid, virus, and other vehicles derived from viral or bacterial sources. In an aspect, one or more of microRNAs of the type disclosed herein is located on a vector that further comprises one or more in vivo expression elements such a promoter element, an enhancer element and a selection element. In an aspect, a gene sequence for expression of a microRNA of the type disclosed herein is operably linked to one or more elements of the vector such as to a promoter element. Introduction of the microRNA to the stem cells may be carried out via any suitable methodology for the introduction of vectors to cells (e.g., gene transfer) such as transfection and transduction. The obtained stem cells once associated with microRNAs of the type disclosed herein (e.g., via culturing or vector introduction) have been restored and are designated restored cells (RC).

In an aspect, the present disclosure contemplates the utilization of microRNAs and/or RCs disclosed herein as compositions for administration to a subject in need thereof. In an aspect, the microRNAs and/or RCs may be a component of a pharmaceutical formulation that is administered locally or systemically to a subject. In an aspect, microRNAs of the type disclosed herein are used in conjunction with a vehicle such as a nanoparticle, micelle, liposome, niosome, microsphere, cyclodextrin and the like. In an aspect, such vehicles further comprise one or more elements to direct the carrier or vehicle to a particular cell, tissue or organ of a subject.

In an aspect, the RCs are administered locally or systemically to a subject in need thereof. The therapeutic processes disclosed herein are generally termed cellular restoration where cells removed from a subject and restored using the methodologies and compositions herein are returned to the subject. In an aspect, this disclosure contemplates treatment of adult stem cells removed from a first subject using the methodologies and compositions disclosed herein and administration of the treated cells (i.e., RCs) to a second subject. This alternative aspect is termed an adoptive cellular restoration therapy. It is also contemplated that in another aspect of the cellular restoration therapy and/or adoptive cellular restoration therapy of this disclosure, the RCs are introduced to a subject that differs in chronological age from the subject who provided the stem cells. Herein the RC and cell-free composition are collectively referred to as restoring agents (RAG).

In some aspects, the appropriate route of administration of a RAG is selected based upon various factors such as the type of medical condition, the underlying cause, the severity of the condition, etc. Suitable routes of administration include, but are not limited to, oral, intravenous, rectal, aerosol, parenteral, ophthalmic, pulmonary, transmucosal, transdermal, vaginal, optic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In some aspects, a RAG is formulated for oral administration, for example, by combining the active agent (e.g., RC) with, e.g., pharmaceutically acceptable carriers or excipients. In various aspects, a RAG such as a cell-free composition is formulated in oral dosage forms that include, by way of example only, tablets, powders, pills, dragees, capsules, liquids, gels, syrups, elixirs, slurries, suspensions and the like.

In other aspects, a RAG is administered topically. Topical administration may be particularly useful for treatment or prevention of scarring resulting from injury or surgery. The RAG may be formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

In some aspects, a RAG is formulated for transdermal administration. Transdermal formulations may employ transdermal delivery devices and transdermal delivery patches and can be lipophilic emulsions or buffered, aqueous solutions, dissolved and/or dispersed in a polymer or an adhesive. In various aspects, such patches are constructed for continuous, pulsatile, or on demand delivery of pharmaceutical agents. In additional aspects, the transdermal delivery of a RAG is accomplished by means of iontophoretic patches and the like. In certain aspects, transdermal patches provide controlled delivery of a RAG. In specific aspects, the rate of absorption is slowed by using rate-controlling membranes or by trapping the compound within a polymer matrix or gel. In alternative aspects, absorption enhancers are used to increase absorption. Absorption enhancers or carriers include absorbable pharmaceutically acceptable solvents that assist passage through the skin. For example, in one aspect, transdermal devices are in the form of a bandage comprising a backing member, a reservoir containing a RAG optionally with carriers, optionally a rate controlling barrier to deliver the compound to the skin of the host at a controlled and predetermined rate over a prolonged period of time, and means to secure the device to the skin.

In other aspects, a RAG is formulated for administration by inhalation. Various forms suitable for administration by inhalation include, but are not limited to, aerosols, mists or powders. RAG are conveniently delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In specific aspects, the dosage unit of a pressurized aerosol is determined by providing a valve to deliver a metered amount. In certain aspects, capsules and cartridges of, such as, by way of example only, gelatins for use in an inhaler or insufflator are formulated containing a powder mix of a RAG and a suitable powder base such as lactose or starch.

As addressed above, other routes of administration, useful for the treatment of particular conditions or delivery to particular cells, tissues, organs, etc. are contemplated. A means of administering the RAG may include, but is not limited to, infusion. Systemically may also include, for example, by a pump, by an intravenous line, or by bolus injection. Bolus injection can include subcutaneous, intramuscular, or intraperitoneal routes.

The phrases "systemic administration" or "administered systemically," as used herein, mean the administration of a compound(s) of the disclosure, composition, drug, or other material such that it enters the subject's system and, thus, is subject to metabolism and other like processes, for example, subcutaneous administration.

In other aspects, the RAG is locally administered by means such as, but not limited to, injection, implantation, grafting, or epicutaneous. For example, the RAG may be administered proximal to a wound site on the subject and functions to ameliorate the symptoms associated with the wound or increase the rate of wound-healing. Administration of the RAG may be conducted in any manner compatible with the compositions disclosed herein and to meet one or more user and/or process goals.

In another aspect, the RAG may be formulated for administration to a subject in order to improve the subject's general health. Such improvements may be identified by quantitative evaluation of one or more physiological or psychological parameters of the subject. In the alternative, such improvements may be identified by the qualitative evaluations of one or more physiological or psychological parameters of the subject.

In an alternative aspect, a subject in administered a RAG may be administered additional active agents as considered beneficial for the treatment of the medical condition. Such additional active agents may be administered concurrent with the administration of the RAG. Examples of additional active agents include but are not limited to: (a) antimicrobials, (b) steroids (e.g., hydrocortisone, triamcinolone); (c) pain medications (e.g., aspirin, an NSAID, and a local anesthetic); (d) anti-inflammatory agents; (e) growth factors; (f) cytokines; (g) hormones; or (h) combinations thereof. Such additional active agents may also be present in a therapeutically effective amount.

Examples of additional active agents for administration with a RAG include, but are not limited to, anesthetics, hypnotics, sedatives and sleep inducers, antipsychotics, antidepressants, antiallergics, antianginals, antiarthritics, antiasthmatics, antidiabetics, antidiarrheal drugs, anticonvulsants, antigout drugs, antihistamines, antipruritics, emetics, antiemetics, antispasmodics, appetite suppressants, neuroactive substances, neurotransmitter agonists, antagonists, receptor blockers and reuptake modulators, beta-adrenergic blockers, calcium channel blockers, disulfuram and disulfuram-like drugs, muscle relaxants, analgesics, antipyretics, stimulants, anticholinesterase agents, parasympathomimetic agents, hormones, anticoagulants, antithrombotics, thrombolytics, immunoglobulins, immunosuppressants, hormone agonists/antagonists, vitamins, antimicrobial agents, antineoplastics, antacids, digestants, laxatives, cathartics, antiseptics, diuretics, disinfectants, fungicides, ectoparasiticides, antiparasitics, heavy metals, heavy metal antagonists, chelating agents, gases and vapors, alkaloids, salts, ions, autacoids, digitalis, cardiac glycosides, antiarrhythmics, antihypertensives, vasodilators, vasoconstrictors, antimuscarinics, ganglionic stimulating agents, ganglionic blocking agents, neuromuscular blocking agents, adrenergic nerve inhibitors, anti-oxidants, vitamins, cosmetics, anti-inflammatories, wound care products, antithrombogenic agents, antitumoral agents, antiangiogenic agents, anesthetics, antigenic agents, wound healing agents, plant extracts, growth factors, emollients, humectants, rejection/anti-rejection drugs, spermicides, conditioners, antibacterial agents, antifungal agents, antiviral agents, antibiotics, tranquilizers, cholesterol-reducing drugs, antitussives, histamine-blocking drugs, monoamine oxidase inhibitor, or combinations thereof.

Specific compounds suitable for use with the RAG include but are not limited to silver sulfadiazine, Nystatin, Nystatin/triamcinolone, Bacitracin, nitrofurazone, nitrofurantoin, a polymyxin (e.g., Colistin, Surfactin, Polymyxin E, and Polymyxin B), doxycycline, antimicrobial peptides (e.g., natural and synthetic origin), NEOSPORIN® (i.e., Bacitracin, Polymyxin B, and Neomycin), POLYSPORIN® (i.e., Bacitracin and Polymyxin B). Additional antimicrobials include topical antimicrobials (i.e., antiseptics), examples of which include silver salts, iodine, benzalkonium chloride, alcohol, hydrogen peroxide, chlorhexidine, acetaminophen; Alfentanil Hydrochloride; Aminobenzoate Potassium; Aminobenzoate Sodium; Anidoxime; Anileridine; Anileridine Hydrochloride; Anilopam Hydrochloride; Anirolac; Antipyrine; Aspirin; Benoxaprofen; Benzydamine Hydrochloride; Bicifadine Hydrochloride; Brifentanil Hydrochloride; Bromadoline Maleate; Bromfenac Sodium; Buprenorphine Hydrochloride; Butacetin; Butixirate; Butorphanol; Butorphanol Tartrate; Carbamazepine; Carbaspirin Calcium; Carbiphene Hydrochloride; Carfentanil Citrate; Ciprefadol Succinate; Ciramadol; Ciramadol Hydrochloride; Clonixeril; Clonixin; Codeine; Codeine Phosphate; Codeine Sulfate; Conorphone Hydrochloride; Cyclazocine; Dexoxadrol Hydrochloride; Dexpemedolac; Dezocine; Diflunisal; Dihydrocodeine Bitartrate; Dimefadane; Dipyrone; Doxpicomine Hydrochloride; Drinidene; Enadoline Hydrochloride; Epirizole; Ergotamine Tartrate; Ethoxazene Hydrochloride; Etofenamate; Eugenol; Fenoprofen; Fenoprofen Calcium; Fentanyl Citrate; Floctafenine; Flufenisal; Flunixin; Flunixin Meglumine; Flupirtine Maleate; Fluproquazone; Fluradoline Hydrochloride; Flurbiprofen; Hydromorphone Hydrochloride; Ibufenac; Indoprofen; Ketazocine; Ketorfanol; Ketorolac Tromethamine; Letimide Hydrochloride; Levomethadyl Acetate; Levomethadyl Acetate Hydrochloride; Levonantradol Hydrochloride; Levorphanol Tartrate; Lofemizole Hydrochloride; Lofentanil Oxalate; Lorcinadol; Lomoxicam; Magnesium Salicylate; Mefenamic Acid; Menabitan Hydrochloride; Meperidine Hydrochloride; Meptazinol Hydrochloride; Methadone Hydrochloride; Methadyl Acetate; Methopholine; Methotrimeprazine; Metkephamid Acetate; Mimbane Hydrochloride; Mirfentanil Hydrochloride; Molinazone; Morphine Sulfate; Moxazocine; Nabitan Hydrochloride; Nalbuphine Hydrochloride; Nalmexone Hydrochloride; Namoxyrate; Nantradol Hydrochloride; Naproxen; Naproxen Sodium; Naproxol; Nefopam Hydrochloride; Nexeridine Hydrochloride; Noracymethadol Hydrochloride; Ocfentanil Hydrochloride; Octazamide; Olvanil; Oxetorone Fumarate; Oxycodone; Oxycodone Hydrochloride; Oxycodone Terephthalate; Oxymorphone Hydrochloride; Pemedolac; Pentamorphone; Pentazocine; Pentazocine Hydrochloride; Pentazocine Lactate; Phenazopyridine Hydrochloride; Phenyramidol Hydrochloride; Picenadol Hydrochloride; Pinadoline; Pirfenidone; Piroxicam Olamine; Pravadoline Maleate; Prodilidine Hydrochloride; Profadol Hydrochloride; Propirarn Fumarate; Propoxyphene Hydrochloride; Propoxyphene Napsylate; Proxazole; Proxazole Citrate; Proxorphan Tartrate; Pyrroliphene Hydrochloride; Remifentanil Hydrochloride; Salcolex; Salethamide Maleate; Salicylamide; Salicylate Meglumine; Salsalate; Sodium Salicylate; Spiradoline Mesylate; Sufentanil; Sufentanil Citrate; Talmetacin; Talniflumate; Talosalate; Tazadolene Succinate; Tebufelone; Tetrydamine; Tifurac Sodium; Tilidine Hydrochloride; Tiopinac; Tonazocine Mesylate; Tramadol Hydrochloride; Trefentanil Hydrochloride; Trolamine; Veradoline Hydrochloride; Verilopam Hydrochloride; Volazocine; Xorphanol Mesylate; Xylazine Hydrochloride; Zenazocine Mesylate; Zomepirac Sodium; Zucapsaicin, Aflyzosin Hydrochloride; Alipamide; Althiazide; Amiquinsin Hydrochloride; Amlodipine Besylate; Amlodipine Maleate; Anaritide Acetate; Atiprosin Maleate; Belfosdil; Bemitradine; Bendacalol Mesylate; Bendroflumethiazide; Benzthiazide; Betaxolol Hydrochloride; Bethanidine Sulfate; Bevantolol Hydrochloride; Biclodil Hydrochloride; Bisoprolol; Bisoprolol Fumarate; Bucindolol Hydrochloride; Bupicomide; Buthiazide: Candoxatril; Candoxatrilat; Captopril; Carvedilol; Ceronapril; Chlorothiazide Sodium; Cicletanine; Cilazapril; Clonidine; Clonidine Hydrochloride; Clopamide; Cyclopenthiazide; Cyclothiazide; Darodipine; Debrisoquin Sulfate; Delapril Hydrochloride; Diapamide; Diazoxide; Dilevalol Hydrochloride; Diltiazem Malate; Ditekiren; Doxazosin Mesylate; Eeadotril; Enalapril Maleate; Enalaprilat; Enalkiren; Endralazine Mesylate; Epithiazide; Eprosartan; Eprosartan Mesylate; Fenoldopam Mesylate; Flavodilol Maleate; Flordipine; Flosequinan; Fosinopril Sodium; Fosinoprilat; Guanabenz; Guanabenz Acetate; Guanacline Sulfate; Guanadrel Sulfate; Guancydine; Guanethidine Monosulfate; Guanethidine Sulfate; Guanfacine Hydrochloride; Guanisoquin Sulfate; Guanoclor Sulfate; Guanoctine Hydrochloride; Guanoxabenz; Guanoxan Sulfate; Guanoxyfen Sulfate; Hydralazine Hydrochloride; Hydralazine Polistirex; Hydroflumethiazide; Indacrinone; Indapamide; Indolaprif Hydrochloride; Indoramin; Indoramin Hydrochloride; Indorenate Hydrochloride; Lacidipine; Leniquinsin; Levcromakalim; Lisinopril; Lofexidine Hydrochloride; Losartan Potassium; Losulazine Hydrochloride; Mebutamate; Mecamylamine Hydrochloride; Medroxalol; Medroxalol Hydrochloride; Methalthiazide; Methyclothiazide; Methyldopa; Methyldopate Hydrochloride; Metipranolol; Metolazone; Metoprolol Fumarate; Metoprolol Succinate; Metyrosine; Minoxidil; Monatepil Maleate; Muzolimine; Nebivolol; Nitrendipine; Ofornine; Pargyline Hydrochloride; Pazoxide; Pelanserin Hydrochloride; Perindopril Erbumine; Phenoxybenzamine Hydrochloride; Pinacidil; Pivopril; Polythiazide; Prazosin Hydrochloride; Primidolol; Prizidilol Hydrochloride; Quinapril Hydrochloride; Quinaprilat; Quinazosin Hydrochloride; Quinelorane Hydrochloride; Quinpirole Hydrochloride; Quinuclium Bromide; Ramipril; Rauwolfia Serpentina; Reserpine; Saprisartan Potassium; Saralasin Acetate; Sodium Nitroprusside; Sulfinalol Hydrochloride; Tasosartan; Teludipine Hydrochloride; Temocapril Hydrochloride; Terazosin Hydrochloride; Terlakiren; Tiamenidine; Tiamenidine Hydrochloride; Tierynafen; Tinabinol; Tiodazosin; Tipentosin Hydrochloride; Trichlormethiazide; Trimazosin Hydrochloride; Trimethaphan Camsylate; Trimoxamine Hydrochloride; Tripamide; Xipamide; Zankiren Hydrochloride; Zofenoprilat Arginine, Alclofenac; Alclometasone Dipropionate; Algestone Acetonide; Alpha Amylase; Ameinafal; Ameinafide; Amfenac Sodium; Amiprilose Hydrochloride; Anakinra; Anirolac; Anitrazafen; Apazone; Balsalazide Disodium; Bendazac;

Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Momiflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Zomepirac Sodium or combinations thereof.

Although the compositions provided herein are principally directed to materials which are suitable for ethical administration to humans, it will be understood by the skilled artisan that such compositions are generally suitable for administration to animals of all sorts. Modification of compositions suitable for administration to humans of the type disclosed herein (i.e., RAGs) in order to render the compositions suitable for administration to various animals can be accomplished by the ordinarily skilled veterinary pharmacologist, with the benefit of this disclosure, who can design and perform such modifications with routine, if any, experimentation. Subjects to which administration of the pharmaceutical compositions of this disclosure is contemplated include, but are not limited to, humans and other primates; mammals including commercially relevant mammals such as cattle, pigs, horses, and sheep; companion animals such as cats and dogs; and birds including commercially relevant birds such as chickens, ducks, geese, and turkeys.

In an aspect, the RAG is formulated for topical administration into forms such as creams, lotions, serums, powders, ointments, or drops. A formulation the RAG for topical administration may also contain pharmaceutically acceptable carriers, moisturizers, oils, fats, waxes, surfactants, thickening agents, antioxidants, viscosity stabilizers, chelating agents, buffers, preservatives, perfumes, dyestuffs, lower alkanols, humectants, emollients, dispersants, sunscreens such as radiation blocking compounds or UV-blockers, antibacterials, antifungals, disinfectants, vitamins, antibiotics, anti-acne agents, as well as other suitable materials that do not have a significant adverse effect on the activity of the topical composition or combinations thereof. Nonlimiting exemplary pharmaceutically acceptable carriers that may be used in the compositions comprising the restored cells may include water, mixtures of water and water-miscible solvents such as lower alkanols or vegetable oils, and water-soluble ophthalmologically acceptable non-toxic polymers (for example, cellulose derivatives such as methylcellulose), glycerin, propylene glycol, methylparaben, alginates, glyceryl stearate, PEG-100 stearate, cetyl alcohol, propylparaben, butylparaben, sorbitols, polyethoxylated anhydrosorbitol monostearate (TWEEN®), white petrolatum (VASELINE®), triethanolamine, emu oil, aloe vera extract, lanolin, cocoa butter, LIPODERM® base, and the like or combinations thereof. In an aspect, the RAG formulated for topical administration may be applied to one or more areas of the skin including the face, hands, and neck.

In an aspect, the methodologies disclosed herein result in therapies that are prophylactic, palliative, curative, or combinations thereof. Methodologies and compositions of the type disclosed herein may be utilized in the treatment of a wide variety of medical conditions related to decreases in cellular function and viability such as age-related medical conditions that include neurological disorders; autoimmune diseases; infectious disease; cancer and disorders associated with radiation overexposure (chronic or acute).

It is contemplated that the methodologies and compositions disclosed herein may result in restored cells having an increased expression of genes associated with improved cellular health with a concomitant decrease in the expression of genes associated with adverse cellular events. In some aspects, the methodologies and compositions disclosed herein result in an increased expression of genes associated with beneficial cellular events.

For example, the methodologies disclosed herein result in a change in the expression patterns for RCs when compared to the adult stem cells from which they were obtained of greater than about 1.5 fold for one or more genes selected from the group consisting of C-abl oncogene-1 non-receptor tyrosine kinase; V-akt murine thymona viral oncogene homolog 1; aldehyde dehydrogenase 1 family, member A3; Ataxia telangiectasia mutated; BMI1 polycomb ring finger oncogene; calrecticulin; cyclin A2; cyclin B1; cyclin D1; cyclin E1; CD44 molecule, cell division cycle 25 homolog C; cyclin-dependent kinase 2; cyclin-dependent kinase 4; cyclin-dependent kinase 6; cyclin-dependent kinase inhibitor 1A; cyclin-dependent kinase inhibitor 1B; cyclin-dependent kinase inhibitor 1C; cyclin-dependent kinase inhibitor 2A; cyclin-dependent kinase inhibitor 2B; cyclin-dependent kinase inhibitor 2C; and cyclin-dependent kinase inhibitor 2D.

In another aspect, RCs may be characterized by an increase in colony-forming ability as measured by a clonogenic assay of equal to or greater than about 5% or alternatively equal to or greater than about 10%.

In another aspect, RCs may be characterized by an increase in cytotoxicity as measured by the number of Natural Killer cells of equal to or greater than about 5% or alternatively equal to or greater than about 10%.

In another aspect, RCs may be characterized by an increase in T-cell activation markers following stimulation with Anti-CD3 and Anti-CD25 monoclonal antibodies as measured by the increase in expression of the activation marker CD25 of equal to or greater than about 5% or alternatively equal to or greater than about 10%.

In another aspect, administration of a RAG of the type disclosed herein to a subject may result in peripheral blood myeloid:lymphoid ratio that is decreased by from about 0.5:1 to about 0.05:1, alternatively from about 0.25:1 to about 0.02:1 or alternatively from about 0.75:1 to about 0.1:1 when compared to the peripheral blood myeloid: lymphoid ratio of the subject prior to introduction of the RAG. Lymphoid lineage cells include T, B, and natural killer (NK) cells, while megakaryocytes and erythrocytes (MegE) as well as granulocytes and macrophages (GM) belong to the myeloid lineage. The peripheral blood myeloid:lymphoid ratio may be determined using any suitable methodology such as phenotyping of blood for the CD33+ versus CD3+CD19 cells.

In another aspect, administration of a RAG of the type disclosed herein to a subject may result in peripheral blood CD4+:CD8+ T-cell ratio that is increased by from about 1:1 to about 3:1, alternatively from about 0.5:1 to about 1:1 or alternatively from about 0.75:1 to about 2:1 when compared to the peripheral blood CD4+:CD8+ T-cell ratio of the subject prior to introduction of the RAG. The peripheral blood CD4+/CD8+ T-cell ratio measures the ratio of T helper cells to cytotoxic T cells. A declining CD4+/CD8+ ratio is associated with ageing and is an indicator of immunosenescence.

In another aspect, administration of a RAG of the type disclosed herein to a subject may result in an increase in peripheral blood T-cell level as measured by the amount of CD3+ cells of equal to or greater than about 5% or alternatively by equal to or greater than about 10% when compared to the peripheral blood T-cell level of the subject prior to introduction of the RAG.

In certain aspects, a therapeutically effective dose of a RAG is delivered to the subject. A therapeutically effective dose will be determined using a variety of factors (e.g., the body weight of the subject) and may be further modified, for example, based on the severity or phase of the medical condition. It is contemplated that the improvements in cellular function observed using the compositions and methodologies disclosed herein will assert positive physiological effects on the function of cells and/or tissues and/or organs and/or the organ systems and/or the organism as a whole. In an aspect, the improvements in cellular function results in a therapeutic effect that ameliorates an adverse medical condition being experienced by the subject.

In an aspect, a subject having been administered a RAG of the type disclosed herein may be subsequently monitored for some time period. Monitoring of the subject may comprise qualitative and quantitative evaluations of the subject's general health and/or medical condition. In some aspects, a subject may be administered a RAG any multiple of times. For example, a subject having been administered a first RAG may display quantitative and/or qualitative improvements in the subject's general health and/or medical condition for some time period. Subsequently, the subject may experience some decline in their general health and/or medical condition and be administered another therapeutically effective of amount of a second RAG. It is contemplated that the composition of the first RAG may be the same as the composition of the second RAG. Alternatively, the composition of the first RAG may differ from the composition of the second RAG.

In some aspects, evaluations of the subject comprise determinations based on analyses disclosed herein (e.g., natural killer assay, telomere length, gene and protein biomarker arrays). In such aspects, the subject may provide a cell sample and the quality of the sample evaluated as disclosed herein. In some aspects, the cell sample quality value at some point post-restoration may be compared to the cell sample quality value pre-restoration and this information utilized to assess whether additional treatment is needed. For example, a subject having a cell sample pre-restoration quality value of 5 may have a cell sample post-restoration quality value of 9 for a time period of up to about 1 year subsequent to the restoration process. The subject's post-restoration cell sample quality value after 1.5 years may have decreased to 7 while after 3 years the value may be 5. In such instances, the subject may be administered another RAG.

EXAMPLES

The following examples are provided to illustrate the present disclosure. The examples are not intended to limit the scope of the present disclosure and they should not be so interpreted.

Example 1

Figure 2:
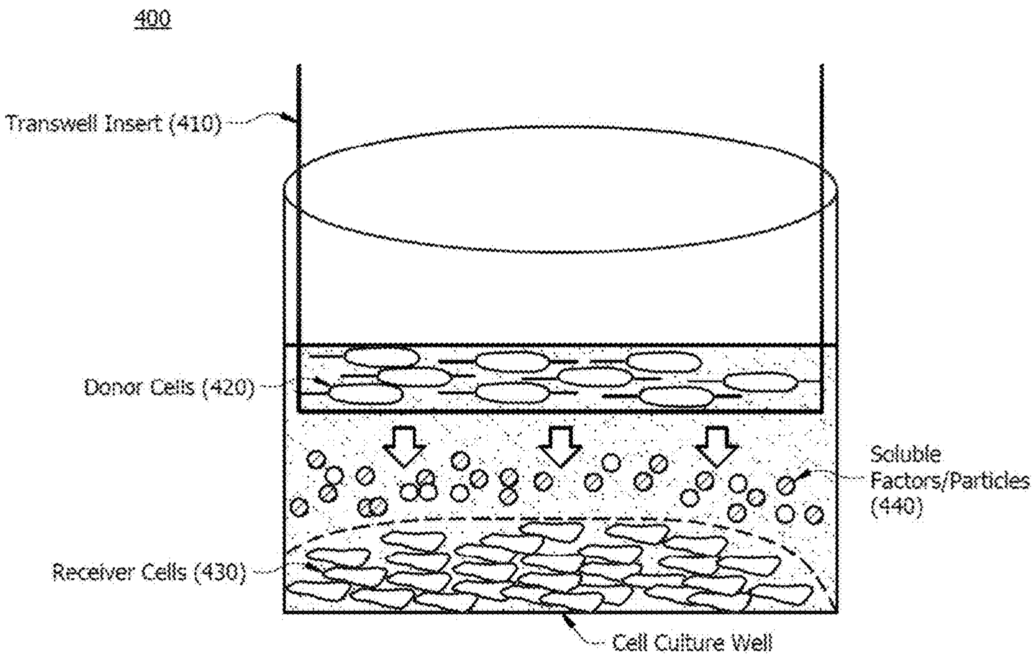
FIG. 2 is a depiction of a transwell coculture apparatus.

A series of transwell experiments were carried out by placing adult stem cells of a donor subject (i.e., donor cells) in the upper chamber of a transwell assembly while the adult stem cells of a receiver subject (i.e. receiver cells) were placed in the lower chamber. Referring to FIG. 2, the transwell culture 400 comprised an insert 410 having a permeable surface that allows the donor cells to uptake and secrete molecules on the basal and/or apical surfaces of the transwell. The transwell insert 410 comprised a permeable membrane with a 0.4 μm pore size. At least a portion of the donor cell sample 420 was applied to the transwell insert 410 while the receiver cell sample 430 was positioned within the lower compartment of the transwell culture with an appropriate amount of culture media.

The donor subjects had an average chronological age of 25 years while the receiver subjects had an average chronological age of 61 years such that the donor subjects' cells are termed juvenile cells and the recipient cells are termed mature cells. The recipient cells following culturing in a transwell in the presence of juvenile cells as described herein are termed heterochronic cells. To the transwell cultures was added either a pharmacological inhibitor of exosome biogenesis GW4869 (3.5 μM) or an inhibitor of exosome packaging BCI-137 (10 μM). BCI-137 is a cell permeable, non-toxic dioxotetrahydroquinoxaline compound that mimics uridine and reversibly interacts with the miRNA binding domain of Argonaute-2 while GW4869 is a cell-permeable non-competitive inhibitor of neutral sphingomyelinase that does not affect acid sphingomyelinase activity. Inhibitors were added to the transwell cultures upon initial seeding (Day 0) and again at Day 3.

Exosomes were collected and quantified to determine the effects of inhibitors on exosome production while RNA extracted from the exosomes were analyzed to determine exosome depletion and levels of RNA depletion. The results are presented in Table 3.

TABLE 3

| Inhibitor | Exosome Production (# exosomes × $10^8$) | Fold Change in ExoRNA SNORD68 | Fold Change in ExoRNA SNORD95 |
|---|---|---|---|
| NONE | 710 | 1 | 1 |
| BCI-137 (10 μM) | 604 | 0.24 | 0.33 |
| GW4869 (3.5 μM) | 558 | 0.43 | 0.67 |

SNORD68 and SNORD95 are small nucleolar RNAs. The results also demonstrated both the BCI-137 and GW4869 effectively depleted miRNAs in exosomes harvested from the heterochronic culture. Further analysis of the effect of the inhibitors on cell function was assessed by determining the total cell vitality, the CD34+ cell vitality and the extent of CD34+ cell expansion. The results demonstrate that the addition of the inhibitor GW4869 appeared toxic to CD34+ cells while BCI-137 elicited no effect on the juvenile or mature cell health. The results demonstrate that inhibition with BCI-137 increased the differentiation potential in the CD34+ mature cells but decreased the differentiation in CD34+ heterochronic cells. The results suggest that mature exosomes and their attendant RNA have a deleterious effect on mature cell function. Further, exosomes and their attendant RNA are implicated in the mechanism of adoptive cell restoration therapy since inhibition by BCI-137 blocked the restorative effects.

Example 2

Exosomes harvested from juvenile cells or heterochronic cells were added to mature cells (10 Million) and subsequently cultured for seven days. Table 4 reports the results on total blood cells, stem cell function, cell expansion and cell vitality for CD34+ cells after 3 and 7 days of culture.

TABLE 4

| Day | Cell Culture Type | Exosome Treatment Type | Exosome Dose to culture × $10^6$ count | CD34+ Differentiation (# CFU-GM) | Total Blood Cells Vitality | CD34+ Cell Expansion (% cells) | CD34+ Cell Vitality |
|---|---|---|---|---|---|---|---|
| 3 | A/A | Y/Y | 1 | 230 | 89.82 | 0.51 | 74.03 |
| 7 | A/A | Y/Y | 10 | 208 | 83 | 0.41 | 59.22 |
| 3 | A/A | Y/Y | 1 | 128 | 90.62 | 0.55 | 64.83 |
| 7 | A/A | Y/Y | 10 | 150 | 81.39 | 0.49 | 50.82 |
| 3 | A/A | A/A | 1 | 166 | 90.87 | 0.51 | 78.72 |
| 7 | A/A | A/A | 10 | 102 | 84.74 | 0.4 | 66.78 |
| 3 | A/A | A/A | 1 | 220 | 90.91 | 0.47 | 80.09 |
| 7 | A/A | A/A | 10 | 56 | 84.82 | 0.3 | 57.63 |
| 3 | A/A | A/Y | 1 | 246 | 90.4 | 0.41 | 77.81 |
| 7 | A/A | A/Y | 10 | 164 | 84.64 | 0.28 | 64.86 |
| 3 | A/A | A/Y | 1 | 28 | 90.05 | 0.49 | 75.38 |
| 7 | A/A | A/Y | 10 | 296 | 85.18 | 0.29 | 73.8 |
| 3 | Y/Y | N/A | N/A | 200 | 86.88 | 0.5 | 67.2 |
| 7 | Y/Y | N/A | N/A | 198 | 90.57 | 0.11 | 50.54 |
| 3 | A/A | N/A | N/A | 76 | 90.03 | 0.46 | 78.3 |
| 7 | A/A | N/A | N/A | 38 | 66.87 | 0.11 | 69.51 |
| 3 | A/Y | N/A | N/A | 104 | 93.4 | 0.49 | 79.74 |
| 7 | A/Y | N/A | N/A | 234 | 69.68 | 0.15 | 46.15 |

The results demonstrate after 7 days culture increased clonogenic potential for aged isochronic cultures supplemented with juvenile or heterochronic exosomes. A dose of 1 million juvenile exosomes per 10 million mature cells appeared to have improved results when compared to a dose of 10 million juvenile exosomes per 10 million mature cells. Further after 7 days of culture an increased frequency of CD34+ cells were observed in all samples supplemented with exosomes. The results also demonstrated increased total cell vitality was observed in all cultures supplemented with the juvenile exosomes. The data suggests that adoptive cell restoration therapy is possible in the absence of transwell culturing.

Example 3

The identity of microRNAs that may be responsible for affecting the cellular restoration were investigated. Stem cells were obtained from five subjects. Subjects R1, R2, and R3 were receiver subjects who were greater than 60 years in age. Subjects D1 and D2 were donor subjects who were less than 30 years old at the time the compositions were obtained. The compositions were obtained from the subjects post mobilization with NEUPOGEN and standard protocols were utilized for obtaining the compositions. The quality of the compositions obtained were analyzed by flow cytometry and clonogenic assays utilizing standard protocols. Transwell experiments of the type disclosed herein were conducted and donor compositions were placed in the upper chamber of a transwell assembly while receiver compositions were placed in the lower chamber and the compositions analyzed at either 3 days or 7 days. Total RNA was extracted from exosomes purified and converted to cDNA for probing 84 miRNAs using the MIFINDER qPCR ARRAY available from Qiagen. Candidate microRNA was confirmed using a fresh culture of stem cells and was further validated intracellularly in juvenile, mature and heterochronic cells.

The amount of exosome production and exosomal RNA content were determined and the results are presented in Table 5.

TABLE 5

| Cell Type | Exosomal Production (# exosomes × $10^8$) | Exosomal RNA Content (Total RNA/exosome) ($ng^{-8}$) |
|---|---|---|
| Mature | 512 | 96 |
| Juvenile | 288 | 267 |
| Heterochronic | 405 | 120 |

Figure 3:
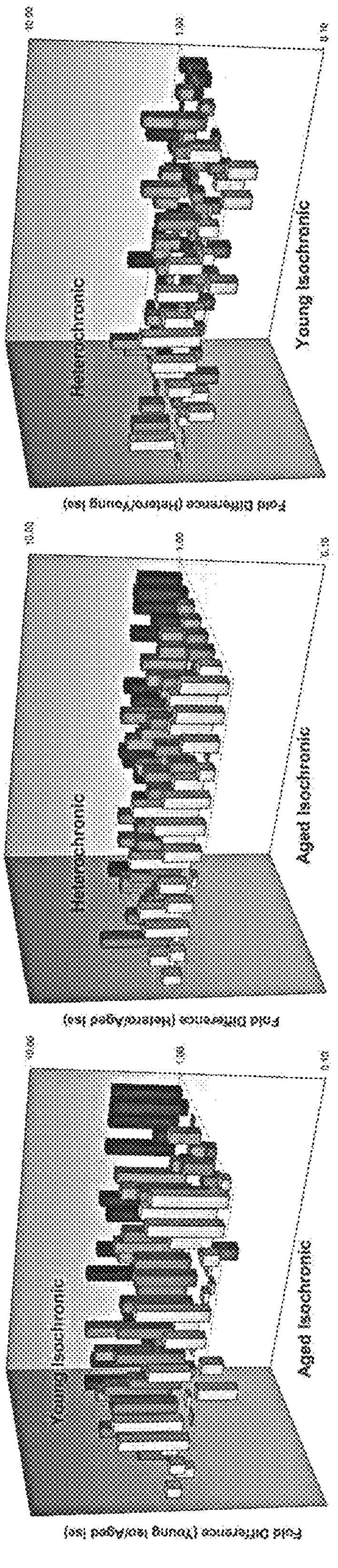
FIG. 3 is a three dimensional exosome profile of microRNAs expressed in different stem cell populations.

Exosomal profiling of 84 commonly expressed micro RNAs is presented in FIG. 3 as a comparison between the different populations studied. The plot demonstrates drastic differences in exosomal microRNA packing in aged versus young cells.

The results also identified a first set of exosomal microRNA candidates whose actions may influence the process of adoptive cell restoration therapy. Specifically miR-146a, miR-103a, miR-106a and miR-19a were validated as exosomal candidates which displayed a trend toward statistical significance after relative quantification of the array. miR-19a demonstrated statistical significance in heterochronic versus mature stem cell populations with p<0.05. Table 6 provides the relative change in the amount of total and intracellular microRNA production for each of the miRs identified.

TABLE 6

| Cell Sample | miR-146a fold change | | miR-103a fold Change | | miR-106b fold change | | miR-19a fold change | |
|---|---|---|---|---|---|---|---|---|
| | Total | IC | Total | IC | Total | IC | Total | IC |
| Mature | 1 | 1 | 1 | 1 | 1 | 1 | 1 | 1 |
| Juvenile | 1.23 | 1.32 | 1.03 | 1.89 | 1.41 | 2.42 | 1.57 | 3.70 |
| Heterochronic | 1.56 | 1.60 | 1.79 | 0.58 | 1.27 | 0.61 | 1.24 | 1.54 |

Candidate microRNAs involved in facilitating adoptive cellular restoration therapy were miR-146a, miR-103a, miR-106a and miR-19a. Combinations of candidate microRNAs were nucleofected at a total concentration of 60 nM into mature blood cells using the CD34+ cell human nucleofector kit (Lonza) and the human CD34+ cell protocol, and effect on CD34+ stem cell vitality and clonogenicity were evaluated compared to siRNA vehicle control. Further, the microRNA combination of miR-103a, miR-106b and miR-19a were nucleofected at a total concentration of 90 nM into mature blood cells using the P3 Primary Cell 4D-Nucleofector X Kit (Lonza) and the human T cell high efficiency protocol, and effect on T cell activation and cell-mediated cytotoxicity were evaluated compared to siRNA vehicle control. Data from these studies are presented in Table 7.

TABLE 7

| Treatment Type | % CD34+ Cell Vitality | CD34+ Differentiation (# CFU-GM) | % CD4+ T Cells | % CD8+ T Cells | % CD4+ T Cell Activation | % CD8+ T Cell Activation | Cytotoxicity (% Target Lysis) |
|---|---|---|---|---|---|---|---|
| No Treatment | 41 | 84 | N/A | N/A | N/A | N/A | N/A |
| siRNA vehicle | 37 | 98 | 4.4 | 1.2 | 89.8 | 92.6 | 42 |
| miR-103a miR-106b miR-19a | 49 | 230 | 12.6 | 2.5 | 95.1 | 95.3 | 46 |
| miR-103a miR-106b miR-19a miR-146a | 32 | 248 | N/A | N/A | N/A | N/A | N/A |
| miR-103a miR-106b miR-146a | 38 | 212 | N/A | N/A | N/A | N/A | N/A |
| miR-103a miR-19a miR-146a | 42 | 218 | N/A | N/A | N/A | N/A | N/A |
| miR-106b miR-19a miR-146a | 37 | 146 | N/A | N/A | N/A | N/A | N/A |

Example 4

Additional candidate microRNAs involved in facilitating adoptive cellular restoration therapy identified were miR-1303, miR-7851-3p, miR-223, miR-4497, miR-619-5p and miR-1273f. Combinations of these additional candidate microRNAs were nucleofected at a total concentration of 60 nM into mature blood cells using the CD34+ cell human nucleofector kit (Lonza) and the human CD34+ cell protocol, and effect on CD34+ clonogenicity was evaluated compared to siRNA vehicle control. Data from these studies are presented in Table 8.

TABLE 8

| Experiment #1 | | Experiment #2 | |
|---|---|---|---|
| Treatment | CD34+ Differentiation (# CFU-GM) | Treatment | CD34+ Differentiation (# CFU-GM) |
| No Treatment | 10 | No Treatment | 38 |
| siRNA vehicle | 20 | siRNA vehicle | 31 |
| miR-223 | 10 | miR-223, miR-4497, miR-1303 | 37 |
| miR-4497 | 20 | miR-619-5p, miR-1273f, miR-7851-3p | 2.5 |
| miR-1303 | 32 | miR-4497, miR-619-5p, miR-7851-3p | 57 |
| miR-619-5p | 46 | miR-223, miR-1303, 1273f | 12 |
| miR-1273f | 9 | N/A | N/A |
| miR-7851-3p | 14 | N/A | N/A |
| miR-223, miR-4497, miR-1303, miR-619-5p, miR-1273f, miR-7851-3p | 4 | N/A | N/A |

The following enumerated aspects are provided as non-limiting examples.

A first aspect which is a method comprising administering to a subject a composition comprising an isolated microRNA having a sequence selected from the group consisting of miR-19a-3p (SEQ ID NO:1); miR-103a-3p (SEQ ID NO:2); miR-106b-5p (SEQ ID NO:3); miR-146a-5p (SEQ ID NO:4); miR-223-5p (SEQ ID NO:5); miR-4497 (SEQ ID NO:6); miR-1303 (SEQ ID NO:7); miR-619-5p (SEQ ID NO:8); miR-1273f (SEQ ID NO:9); miR-7851-3p (SEQ ID NO:10); a functional variant thereof and combinations thereof.

A second aspect which is the method of the first aspect wherein the isolated microRNA is selected from a group consisting of an oligonucleotide having at least about 65% sequence identity with SEQ ID NO:1; an oligonucleotide having at least 65% sequence identity with SEQ ID NO:2; an oligonucleotide having at least 65% sequence identity with SEQ ID NO:3; an oligonucleotide having at least 65% sequence identity with SEQ ID NO:4; an oligonucleotide having at least 65% sequence identity with SEQ ID NO:5; an oligonucleotide having at least 65% sequence identity with SEQ ID NO:6; an oligonucleotide having at least 65% sequence identity with SEQ ID NO:7; an oligonucleotide having at least 65% sequence identity with SEQ ID NO:8; an oligonucleotide having at least 65% sequence identity with SEQ ID NO:9; an oligonucleotide having at least 65% sequence identity with SEQ ID NO:10; and combinations thereof.

A third aspect which is the method of any of the first through second aspects wherein the isolated microRNA is a mimic comprising an oligonucleotide having at least about 65% sequence identity with SEQ ID NO:1; an oligonucleotide having at least 65% sequence identity with SEQ ID NO:2; an oligonucleotide having at least 65% sequence identity with SEQ ID NO:3; an oligonucleotide having at least 65% sequence identity with SEQ ID NO:4; an oligonucleotide having at least 65% sequence identity with SEQ ID NO:5; an oligonucleotide having at least 65% sequence identity with SEQ ID NO:6; an oligonucleotide having at least 65% sequence identity with SEQ ID NO:7; an oligonucleotide having at least 65% sequence identity with SEQ ID NO:8; an oligonucleotide having at least 65% sequence identity with SEQ ID NO:9; an oligonucleotide having at least 65% sequence identity with SEQ ID NO:10; and combinations thereof.

A fourth aspect which is the method of the first aspect wherein the composition comprises miR-19a-3p (SEQ ID NO:1); miR-103a-3p (SEQ ID NO:2); miR-106b-5p (SEQ ID NO:3); miR-146a-5p (SEQ ID NO:4); a functional variant thereof or combinations thereof.

A fifth aspect which is the method the first aspect wherein the composition comprises miR-19a-3p (SEQ ID NO:1); a mimic thereof, a functional variant thereof or combinations thereof A sixth aspect which is the method of any of the first through fifth aspects wherein the composition further comprises a vehicle.

A seventh aspect which is the method of the sixth aspect wherein the vehicle comprises a nanoparticle, micelles, liposome, niosomes, microspheres, cyclodextrins or combinations thereof.

An eighth aspect which is a method of preparing a restored stem cell comprising i) obtaining a sample comprising adult stem cells; ii) culturing the sample in the presence of an isolated microRNA having a sequence selected from the group consisting of miR-19a-3p (SEQ ID NO:1); miR-103a-3p (SEQ ID NO:2); miR-106b-5p (SEQ ID NO:3); miR-146a-5p (SEQ ID NO:4); miR-223-5p (SEQ ID NO:5); miR-4497 (SEQ ID NO:6); miR-1303 (SEQ ID NO:7); miR-619-5p (SEQ ID NO:8); miR-1273f (SEQ ID NO:9); miR-7851-3p (SEQ ID NO:10); a functional variant thereof; and combinations thereof to produce the restored stem cells; and iii) recovering the restored stem cells from the sample wherein the restored stem cells when compared to the adult stem cells are characterized by a change in expression of greater than about 1.5 fold for one or more genes selected from the group consisting of C-abl oncogene-1 non-receptor tyrosine kinase; V-akt murine thymona viral oncogene homolog 1; aldehyde dehydrogenase 1 family, member A3; Ataxia telangiectasia mutated; BMI1 polycomb ring finger oncogene; calrecticulin; cyclin A2; cyclin B1; cyclin D1; cyclin E1; CD44 molecule, cell division cycle 25 homolog C; cyclin-dependent kinase 2; cyclin-dependent kinase 4; cyclin-dependent kinase 6; cyclin-dependent kinase inhibitor 1A; cyclin-dependent kinase inhibitor 1B; cyclin-dependent kinase inhibitor 1C; cyclin-dependent kinase inhibitor 2A; cyclin-dependent kinase inhibitor 2B; cyclin-dependent kinase inhibitor 2C; and cyclin-dependent kinase inhibitor 2D.

A ninth aspect which is the method of the eighth aspect further comprising contacting the restored cells with carriers, excipients, stabilizers, antioxidants, polypeptides, proteins, hydrophilic polymers, amino acids, carbohydrates, chelating agents, sugar alcohols salt-forming counterions, nonionic surfactants or combinations thereof to form a pharmaceutical formulation.

A tenth aspect which is the method of the eighth through ninth aspects further comprising administering the pharmaceutical formulation to a subject in need thereof.

An eleventh aspect which is the method of the tenth aspect wherein the subject has a peripheral blood myeloid:lymphoid ratio that is decreased by from about 0.5:1 to about 0.05:1, when compared to the peripheral blood myeloid:lymphoid ratio of the subject prior to administration of the pharmaceutical formulation.

A twelfth aspect which is the method of any of the tenth through eleventh aspects wherein the subject has a peripheral blood CD4+:CD8+ T-cell ratio that is increased by about 1:1 to about 3:1, when compared to the peripheral blood CD4+:CD8+ T-cell ratio of the subject prior to administration of the pharmaceutical formulation.

A thirteenth aspect which is a method of preparing a restored stem cell composition comprising (i) obtaining a cell sample comprising adult stem cells; (ii) introducing a vector construct containing a nucleic acid sequence for expression of an isolated microRNA having a sequence selected from the group consisting of miR-19a-3p (SEQ ID NO:1); miR-103a-3p (SEQ ID NO:2); miR-106b-5p (SEQ ID NO:3); miR-146a-5p (SEQ ID NO:4); miR-223-5p (SEQ ID NO:5); miR-4497 (SEQ ID NO:6); miR-1303 (SEQ ID NO:7); miR-619-5p (SEQ ID NO:8); miR-1273f (SEQ ID NO:9); miR-7851-3p (SEQ ID NO:10); a functional variant thereof; and combinations thereof into the adult stem cells to produce restored stem cells; and (iii) recovering the restored stem cells.

A fourteenth aspect which is the method of the thirteenth aspect wherein the vector comprises a promoter sequence operably linked to the microRNA.

A fifteenth aspect which is the method of any of the thirteenth through fourteenth aspects wherein the restored stem cells constitutively express the isolated microRNA.

A sixteenth aspect which is the method of any of the thirteenth through fourteenth aspects wherein the restored stem cells inducibly express the isolated microRNA.

A seventeenth aspect which is the method of any of the thirteenth through sixteenth aspects further comprising administering the restored stem cells to a subject in need thereof.

An eighteenth aspect which is a pharmaceutical formulation comprising an adult stem cell wherein the adult stem cell comprises a plasmid containing a promoter element operably linked to an oligonucleotide for expression of a microRNA having a sequence selected from the group consisting of miR-19a-3p (SEQ ID NO:1); miR-103a-3p (SEQ ID NO:2); miR-106b-5p (SEQ ID NO:3); miR-146a-5p (SEQ ID NO:4); miR-223-5p (SEQ ID NO:5); miR-4497 (SEQ ID NO:6); miR-1303 (SEQ ID NO:7); miR-619-5p (SEQ ID NO:8); miR-1273f (SEQ ID NO:9); miR-7851-3p (SEQ ID NO:10); a functional variant thereof and combinations thereof.

A nineteenth aspect which is a pharmaceutical formulation comprising an isolated microRNA selected from the group consisting of miR-19a-3p (SEQ ID NO:1); miR-103a-3p (SEQ ID NO:2); miR-106b-5p (SEQ ID NO:3); miR-146a-5p (SEQ ID NO:4); miR-223-5p (SEQ ID NO:5); miR-4497 (SEQ ID NO:6); miR-1303 (SEQ ID NO:7); miR-619-5p (SEQ ID NO:8); miR-1273f (SEQ ID NO:9); miR-7851-3p (SEQ ID NO:10); a functional variant thereof; and combinations thereof.

A twentieth aspect which is the formulation of the nineteenth aspect wherein the isolated microRNAs comprise miR-4497 (SEQ ID NO:6); miR-619-5p (SEQ ID NO:8); miR-7851-3p (SEQ ID NO:10); a functional variant thereof; or combinations thereof.

A twenty-first aspect which is the formulation of any of the eighteenth through twentieth aspects further comprising carriers, excipients, stabilizers, antioxidants, polypeptides, proteins, hydrophilic polymers, amino acids, carbohydrates, chelating agents, sugar alcohols salt-forming counterions, nonionic surfactants or combinations thereof to form the pharmaceutical formulation.

A twenty-second aspect which is a kit comprising the formulation of any of the eighteenth through twenty-first aspects.

For the purpose of any U.S. national stage filing from this application, all publications and patents mentioned in this disclosure are incorporated herein by reference in their entireties, for the purpose of describing and disclosing the constructs and methodologies described in those publications, which might be used in connection with the methods of this disclosure. Any publications and patents discussed above and throughout the text are provided solely for their disclosure prior to the filing date of the present application. Nothing herein is to be construed as an admission that the inventors are not entitled to antedate such disclosure by virtue of prior invention.

Unless indicated otherwise, when a range of any type is disclosed or claimed, for example a range of the number of carbon atoms, molar ratios, temperatures, and the like, it is intended to disclose or claim individually each possible number that such a range could reasonably encompass, including any sub-ranges encompassed therein. Moreover, when a range of values is disclosed or claimed, which Applicants intent to reflect individually each possible number that such a range could reasonably encompass, Applicants also intend for the disclosure of a range to reflect, and be interchangeable with, disclosing any and all sub-ranges and combinations of sub-ranges encompassed therein. Accordingly, Applicants reserve the right to proviso out or exclude any individual members of any such group, including any sub-ranges or combinations of sub-ranges within the group, if for any reason Applicants choose to claim less than the full measure of the disclosure, for example, to account for a reference that Applicants are unaware of at the time of the filing of the application.

In any application before the United States Patent and Trademark Office, the Abstract of this application is provided for the purpose of satisfying the requirements of 37 C.F.R. § 1.72 and the purpose stated in 37 C.F.R. § 1.72(b) "to enable the United States Patent and Trademark Office and the public generally to determine quickly from a cursory inspection the nature and gist of the technical disclosure." Therefore, the Abstract of this application is not intended to be used to construe the scope of the claims or to limit the scope of the subject matter that is disclosed herein. Moreover, any headings that can be employed herein are also not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

The invention claimed is:

1. A pharmaceutical formulation comprising:
a pharmaceutically acceptable excipient;
an expressible miR-619-5p (SEQ ID NO: 8) microRNA located on a vector that comprises one or more expression elements, wherein the expressible miR-619-5p microRNA is operably linked to the one or more expression elements; and
an expressible miR-4497 (SEQ ID NO: 6) microRNA or an expressible miR-1303 (SEQ ID NO: 7) microRNA, or both.

2. A pharmaceutical formulation comprising:
a pharmaceutically acceptable excipient;
an expressible miR-619-5p (SEQ ID NO: 8) microRNA located on a vector that comprises one or more expression elements, wherein the expressible miR-619-5p microRNA is operably linked to the one or more expression elements; and wherein the vector further comprises an expressible miR-4497 (SEQ ID NO: 6) microRNA or an expressible miR-1303 (SEQ ID NO: 7) microRNA, or both.

3. The pharmaceutical formulation of claim 1, further comprising carriers, excipients, stabilizers, antioxidants, polypeptides, proteins, hydrophilic polymers, amino acids, carbohydrates, chelating agents, sugar alcohols salt-forming counterions, nonionic surfactants or combinations thereof.

4. The pharmaceutical formulation of claim 1, further comprising a vehicle.

5. The pharmaceutical formulation of claim 4, wherein the vehicle comprises a nanoparticle, micelles, liposome, niosomes, microspheres, cyclodextrins or combinations thereof.

6. The pharmaceutical formulation of claim 1, wherein the pharmaceutical formulation is formulated for oral, intravenous, rectal, aerosol, parenteral, intramuscular, subcutaneous, intramedullary, intrathecal, direct intraventricular, intraperitoneal, intralymphatic, intranasal, ophthalmic, pulmonary, transmucosal, transdermal, vaginal, optic, nasal, or topical administration.

7. The pharmaceutical formulation of claim 1, wherein the pharmaceutical formulation is formulated to be administered with an additional active agent, wherein the additional active agent comprises anesthetics, hypnotics, sedatives and sleep inducers, antipsychotics, antidepressants, antiallergics, antianginals, antiarthritics, antiasthmatics, antidiabetics, antidiarrheal drugs, anticonvulsants, antigout drugs, antihistamines, antipruritics, emetics, antiemetics, antispasmodics, appetite suppressants, neuroactive substances, neurotransmitter agonists, antagonists, receptor blockers and reuptake modulators, beta-adrenergic blockers, calcium channel blockers, disulfuram and disulfuram-like drugs, muscle relaxants, analgesics, antipyretics, stimulants, anticholinesterase agents, parasympathomimetic agents, hormones, anticoagulants, antithrombotics, thrombolytics, immunoglobulins, immunosuppressants, hormone agonists/antagonists, vitamins, antimicrobial agents, antineoplastics, antacids, digestants, laxatives, cathartics, antiseptics, diuretics, disinfectants, fungicides, ectoparasiticides, antiparasitics, heavy metals, heavy metal antagonists, chelating agents, gases and vapors, alkaloids, salts, ions, autacoids, digitalis, cardiac glycosides, antiarrhythmics, antihypertensives, vasodilators, vasoconstrictors, antimuscarinics, ganglionic stimulating agents, ganglionic blocking agents, neuromuscular blocking agents, adrenergic nerve inhibitors, anti-oxidants, vitamins, cosmetics, anti-inflammatories, wound care products, antithrombogenic agents, antitumoral agents, antiangiogenic agents, anesthetics, antigenic agents, wound healing agents, plant extracts, growth factors, emollients, humectants, rejection/anti-rejection drugs, spermicides, conditioners, antibacterial agents, antifungal agents, antiviral agents, antibiotics, tranquilizers, cholesterol-reducing drugs, antitussives, histamine-blocking drugs, monoamine oxidase inhibitor, or combinations thereof.

8. The pharmaceutical formulation of claim 2, further comprising carriers, excipients, stabilizers, antioxidants, polypeptides, proteins, hydrophilic polymers, amino acids, carbohydrates, chelating agents, sugar alcohols salt-forming counterions, nonionic surfactants or combinations thereof.

9. The pharmaceutical formulation of claim 2, further comprising a vehicle.

10. The pharmaceutical formulation of claim 9, wherein the vehicle comprises a nanoparticle, micelles, liposome, niosomes, microspheres, cyclodextrins or combinations thereof.

11. The pharmaceutical formulation of claim 2, wherein the pharmaceutical formulation is formulated for oral, intravenous, rectal, aerosol, parenteral, intramuscular, subcutaneous, intramedullary, intrathecal, direct intraventricular, intraperitoneal, intralymphatic, intranasal, ophthalmic, pulmonary, transmucosal, transdermal, vaginal, optic, nasal, or topical administration.

12. The pharmaceutical formulation of claim 2, wherein the pharmaceutical formulation is formulated to be administered with an additional active agent, wherein the additional active agent comprises anesthetics, hypnotics, sedatives and sleep inducers, antipsychotics, antidepressants, antiallergics, antianginals, antiarthritics, antiasthmatics, antidiabetics, antidiarrheal drugs, anticonvulsants, antigout drugs, antihistamines, antipruritics, emetics, antiemetics, antispasmodics, appetite suppressants, neuroactive substances, neurotransmitter agonists, antagonists, receptor blockers and reuptake modulators, beta-adrenergic blockers, calcium channel blockers, disulfuram and disulfuram-like drugs, muscle relaxants, analgesics, antipyretics, stimulants, anticholinesterase agents, parasympathomimetic agents, hormones, anticoagulants, antithrombotics, thrombolytics, immunoglobulins, immunosuppressants, hormone agonists/antagonists, vitamins, antimicrobial agents, antineoplastics, antacids, digestants, laxatives, cathartics, antiseptics, diuretics, disinfectants, fungicides, ectoparasiticides, antiparasitics, heavy metals, heavy metal antagonists, chelating agents, gases and vapors, alkaloids, salts, ions, autacoids, *digitalis*, cardiac glycosides, antiarrhythmics, antihypertensives, vasodilators, vasoconstrictors, antimuscarinics, ganglionic stimulating agents, ganglionic blocking agents, neuromuscular blocking agents, adrenergic nerve inhibitors, antioxidants, vitamins, cosmetics, anti-inflammatories, wound care products, antithrombogenic agents, antitumoral agents, antiangiogenic agents, anesthetics, antigenic agents, wound healing agents, plant extracts, growth factors, emollients, humectants, rejection/anti-rejection drugs, spermicides, conditioners, antibacterial agents, antifungal agents, antiviral agents, antibiotics, tranquilizers, cholesterol-reducing drugs, antitussives, histamine-blocking drugs, monoamine oxidase inhibitor, or combinations thereof.

* * * * *